United States Patent
Pierson

(10) Patent No.: US 10,449,083 B2
(45) Date of Patent: *Oct. 22, 2019

(54) INCONTINENCE COLLECTION DEVICE AND RELATED METHODS

(71) Applicant: Kenneth Pierson, Visalia, CA (US)

(72) Inventor: Kenneth Pierson, Visalia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/973,537

(22) Filed: May 8, 2018

(65) Prior Publication Data

US 2018/0256386 A1 Sep. 13, 2018

Related U.S. Application Data

(63) Continuation of application No. 15/289,065, filed on Oct. 7, 2016, now Pat. No. 10,016,299.

(51) Int. Cl.
| | | |
|---|---|---|
| *A61M 5/32* | (2006.01) | |
| *A61F 5/44* | (2006.01) | |
| *A61F 5/453* | (2006.01) | |
| *A61F 5/441* | (2006.01) | |
| *A61M 1/00* | (2006.01) | |
| *A61M 27/00* | (2006.01) | |

(52) U.S. Cl.
CPC .............. *A61F 5/453* (2013.01); *A61F 5/44* (2013.01); *A61F 5/441* (2013.01); *A61F 5/4404* (2013.01); *A61F 5/4405* (2013.01); *A61F 5/4407* (2013.01); *A61F 5/4408* (2013.01)

(58) Field of Classification Search
CPC .......... A61M 5/32; A61M 1/00; A61M 27/00; A61F 5/44; A61B 19/00
See application file for complete search history.

(56) References Cited

U.S. PATENT DOCUMENTS

| | | |
|---|---|---|
| 205,566 A | 7/1878 | Miller |
| 274,447 A | 3/1883 | Kennish |
| 549,678 A | 11/1895 | Miller |
| 844,755 A | 2/1907 | Schalow |
| 936,186 A | 10/1909 | Tellerson |
| 1,014,465 A | 6/1911 | Hall |
| 1,602,047 A | 10/1926 | Schultheis |
| 1,730,330 A | 10/1929 | Meserve |
| 2,121,354 A | 6/1938 | Goodwin |
| 2,803,251 A | 8/1957 | White |
| 2,836,963 A | 6/1958 | Fox |
| 2,926,885 A | 3/1960 | Pugi et al. |
| 3,035,299 A | 5/1962 | Gordon et al. |
| 3,087,656 A | 4/1963 | Dougherty |
| 3,227,173 A | 1/1966 | Bernstein |
| 3,273,402 A | 9/1966 | Farr |
| 3,534,771 A | 10/1970 | Homer et al. |
| 3,739,783 A | 6/1973 | Broerman |
| 4,078,578 A | 3/1978 | Buchholz |
| 4,133,457 A | 1/1979 | Klassen |
| 4,492,246 A | 1/1985 | Prescott et al. |
| 4,627,958 A | 12/1986 | Hays |
| 4,640,493 A | 2/1987 | Dudzik |

(Continued)

*Primary Examiner* — Tatyana Zalukaeva
*Assistant Examiner* — Ilya Y Treyger
(74) *Attorney, Agent, or Firm* — William K. Nelson; Mark D. Miller; Jared E. Christensen

(57) ABSTRACT

An external incontinence collection device that includes a novel one-way valve system for preventing backflow from a collection receptacle. The incontinence collection device also includes novel drainage valve structures that improve the drainage functionality.

23 Claims, 26 Drawing Sheets

(56) References Cited

U.S. PATENT DOCUMENTS

| | | | |
|---|---|---|---|
| 4,846,816 | A | 7/1989 | Manfredi |
| 4,863,144 | A | 9/1989 | Wilson et al. |
| 4,966,483 | A | 10/1990 | Hashimoto et al. |
| 5,394,715 | A | 3/1995 | Guerette |
| 5,413,311 | A | 5/1995 | Arstein |
| 5,741,240 | A | 4/1998 | Olsen |
| 5,816,457 | A | 10/1998 | Croft |
| 6,024,252 | A | 2/2000 | Clyde |
| 6,409,406 | B1 | 6/2002 | Schwartzman |
| 6,764,064 | B2 | 7/2004 | Sturm et al. |
| 6,886,807 | B1 | 5/2005 | Gill |
| 7,264,141 | B2 | 9/2007 | Patel et al. |
| 7,322,491 | B2 | 1/2008 | Py et al. |
| 8,152,138 | B2 | 4/2012 | Skillern |
| 9,423,041 | B2 | 8/2016 | Py |
| 2008/0051763 | A1 | 2/2008 | Frojd |

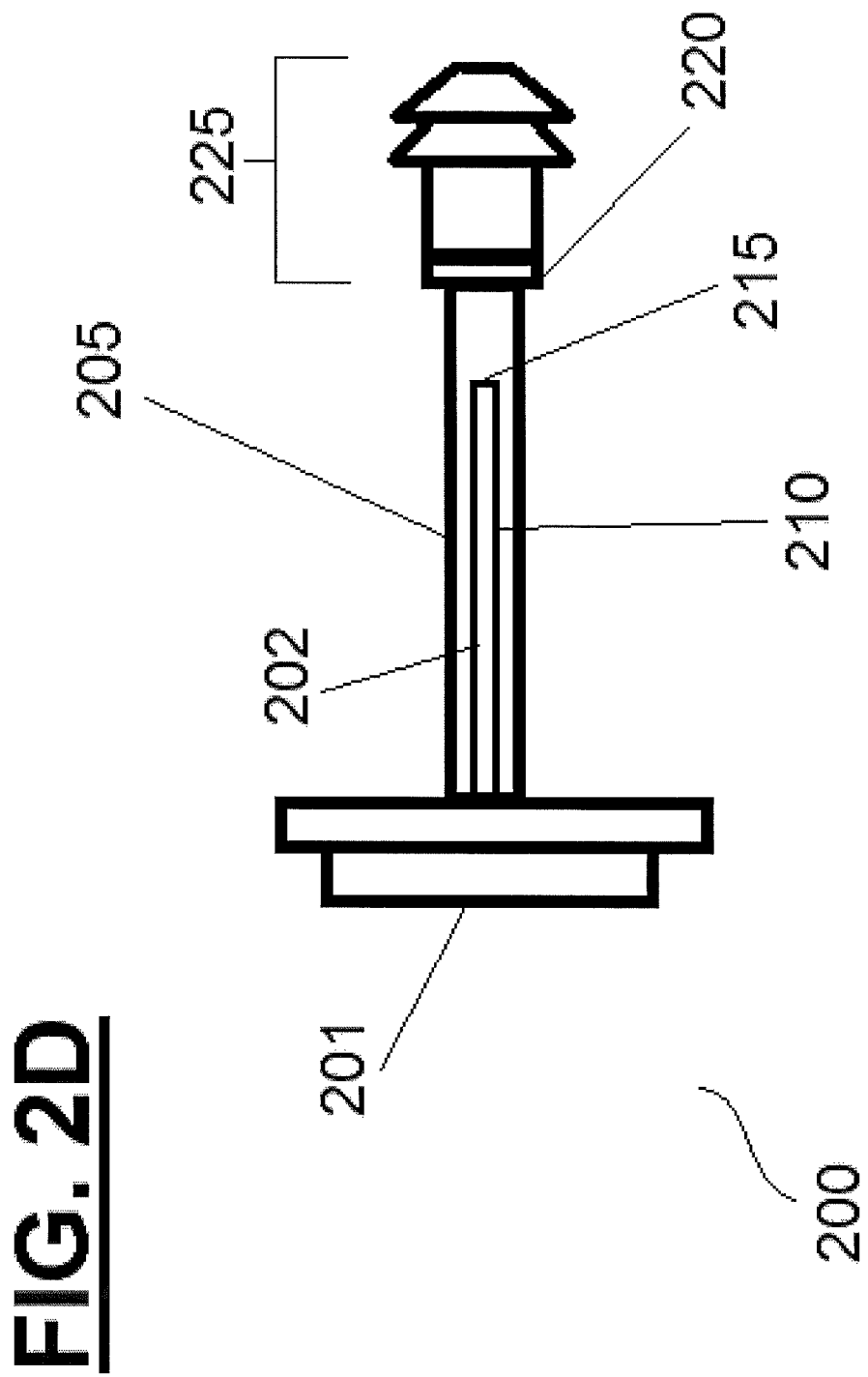

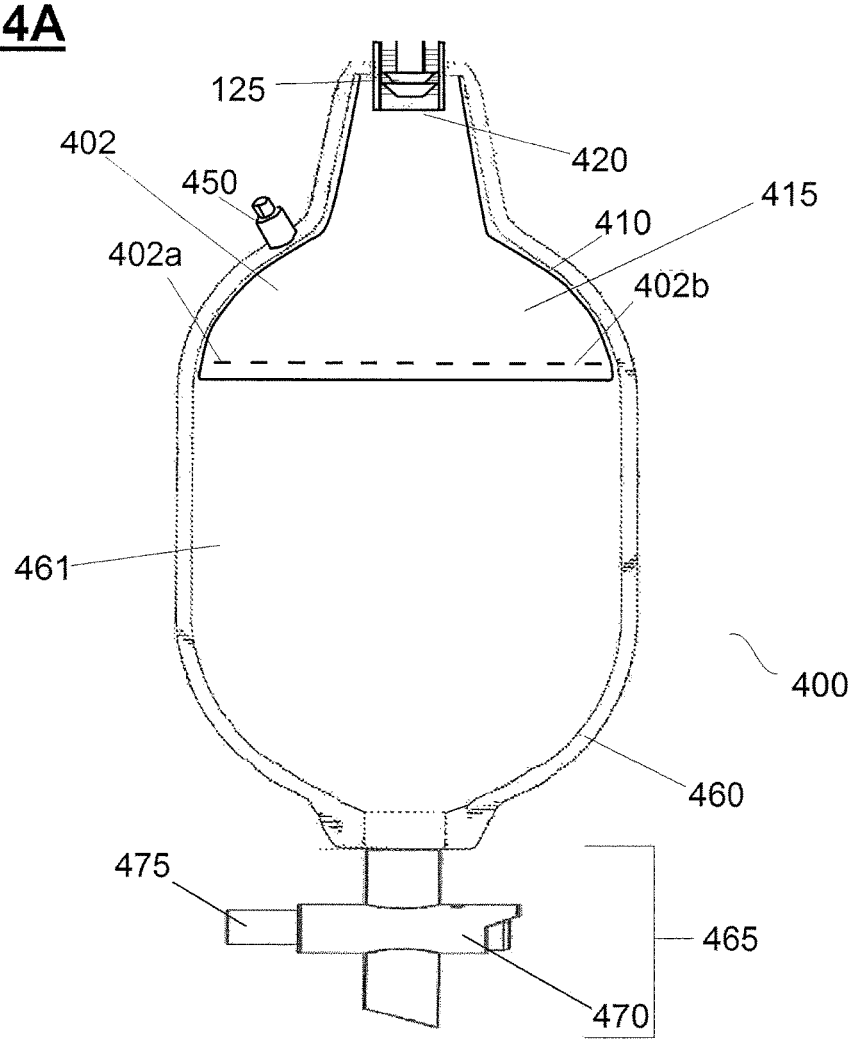

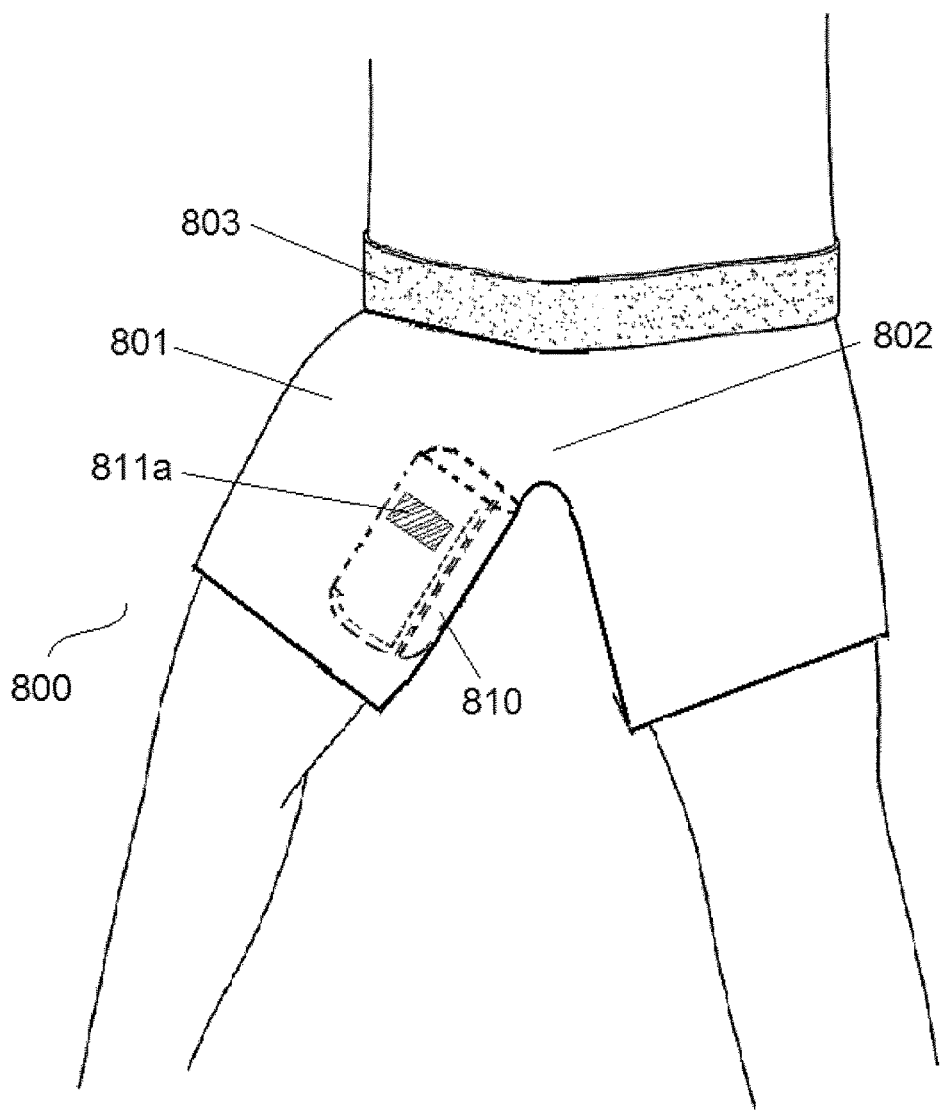

INCONTINENCE COLLECTION DEVICE AND RELATED METHODS

FIELD OF THE INVENTION

The present invention relates to external incontinence collection devices and methods for using the same. More specifically, the embodiments of the present invention pertain to external incontinence collection devices that may include one-way valve structures for controlling backflow and/or novel drainage valves.

DISCUSSION OF THE BACKGROUND

Male urinary incontinence is a common medical problem. Commonly used male urinary incontinence devices include absorbent diapers, invasive urinary catheters and/or external, non-invasive urine collection devices. Each device either subjects the user to adverse health issues. For example, diapers are associated with a high rate of skin breakdown and ulcer formation while indwelling urinary catheters are a cause of urinary tract infections (UTI). Accordingly, there is a great demand for non-invasive external incontinence devices for collecting urine from males without that does not cause skin break down or UTI.

Urine collection devices are typically attached to or inserted into a user's body for the purpose of collecting urine or allowing the user to void the bladder. The present devices in the field include, but are not limited to, urinary catheters, Foley catheters, suprapubic catheters, nephrostomy catheters, condom catheters, and external incontinence devices. Of these devices, conventional incontinence devices may collect urine excreted from into a urine collection bag or may enable the user to immediately void the user's bladder. More recently a line of products have come out to address the need for a urinary incontinence device for males that attaches externally, however, there are issues with the current devices.

Current external urine collection devices have incorporated a parameatal seal to be adhesively secured to the end of the glans penis to prevent leakage of urine. One prominent issue with the current seal is that users incorrectly attach the device resulting in the urine leakage. The addition of multiple attachment members, such as a plurality of petals in addition to a strap, has been used to try and address the problem. However, additional attachment member(s) has not solved the problem. For users, multiple attachment members may increase the likelihood of creating a poor seal resulting in urine leakage, requiring the reattachment or replacement of the attachment members.

Even with the attachment members optimally positioned and attached, the attachment members may fail due to backflow of urine to the attachment members, which can cause detachment of the incontinence collection device. The adhesive attaching the device to the user is dissolved when subjected to a warm liquid. In current devices, the collection conduit that collects excreted urine does not adequately prevent backflow. Conventional devices allow urine to flow back into the collection conduit and come in contact with the dissolvable adhesive. Due to the fact that urine is warm, upon backflow of urine, the adhesive may dissolve leading to the detachment of the device from the user and urine spillage. For example, one may dissolve the adhesive by simply tilting the device towards the collection conduit (e.g., by leaning back, reclining in a chair, crossing a leg, etc.). Thus, common acts may lead to the backflow of urine and failure of the adhesive, resulting in detachment of the incontinence device.

Yet another issue with the current external male incontinence device is the drainage valve. Often times the drainage valve is a snap-fit valve (similar to the basic air retention valves found in inflatable mattresses, flotation devices, and pool toys). The user has to disengage the exit valve manually by removing the cap of the snap-fit valve to release the urine collected in the urine receptacle. It is difficult for a user to control the flow of urine when initially opening the snap-fit valve cap because the valves are clumsy and awkward and require two hands to operate. Therefore, the user may spill urine onto their hands or other undesirable places when trying to empty the urine receptacle when opening the snap-fit exit valve.

Therefore, it is desirable to have an improved incontinence collection device and methods for using the same.

SUMMARY OF THE INVENTION

The present invention is directed to embodiments of incontinence collection devices that may include valve structures for preventing backflow of urine and/or a valve structure that allows for a controlled and cleanly drainage of urine from the device. The features of the present embodiments provide for improved urine collection and storage over conventional devices, allowing the user to avoid detachment of the device, urine spillage, and clumsy drainage of the device. The embodiments of the present invention also include methods of operation and use of the incontinence collection devices of the present invention. Discussion of the features of the incontinence collection devices of the present invention are provided below.

The incontinence collection devices of the present invention may include an innovative attachment structure that improves sealing between the incontinence device and the penis, making the attachment easier and helping to prevent or reduce the risk of detachment of the incontinence device. In some embodiments, the attachment structure may include a concave, flexible receiver for placement on the end of the user's penis where urine is excreted (e.g., the glans penis). The concave receiver may be shaped to approximate the shape of the glans penis or a portion thereof. The concave receiver may be made from a polymer material such as a silicone rubber, polyurethane rubber, non-vulcanized natural rubber, polystyrene rubbers, polychloroprene, non-latex rubber materials (e.g., nitrile), and other sturdy, flexible materials that can safely contact the skin. The flexibility of the concave receiver may allow for accommodation of variations in anatomy. The concave receiver may also include a collection hole (e.g., an elliptical hole) to allow urine to pass from the concave receiver to a collection conduit in fluid communication with the concave receiver. The collection hole may be surrounded by a raised bead (a rim or lip, e.g., having an elliptical or oblong perimeter) that may be positioned to abut the glans penis and surround the external urethral orifice (urethral meatus), such that as urine is excreted it is captured within the raised bead and is prevented from flowing to peripheral portions of the concave receiver that are exterior to the raised bead. The interior surface of the concave receiver may be coated with an adhesive to allow the concave receiver to be adhered to the glans penis and seal concave receiver to the glans penis such that urine is directed into the collection hole of the concave receiver. In the process of adhering the concave receiver to the glans penis, the raised bead and the collection hole may be aligned with the exterior urethral orifice, such that urine is directly and efficiently drained through the collection hole. The collection hole may be in fluid communication with a collection conduit that receives urine passing through the collection hole.

In some embodiments, the attachment member may also have a one or more adhesive flaps or tabs that may aid in attaching the incontinence collection device to the penis. These adhesive flaps or tabs may include an adhesive on side thereof to allow them to be adhered to the skin of the penis (e.g., on the glans penis and/or the body of the penis). In some embodiments, the adhesive flaps may be attached to the outer side of the concave receiver, providing adhesion attachment strength for the incontinence collection device. In some implementations, the adhesive flaps may radiate out from the concave receiver like petals, allowing the flaps to provide further adhesion around the circumference of the penis. In other embodiments, the device may include an adhesive bandage structure having a central adhesive pad with adhesive flaps radiating out from the central adhesive pad, with no concave receiver included. In such embodiments, a collection disk may be provided in the central adhesive pad. The collection disk may include a collection hole therein for receiving urine from the external urethral orifice.

In some embodiments, the attachment member may also have an adhesive strap that may aid in attaching the incontinence collection device to the penis. The adhesive strap may include an adhesive on one side thereof to allow the strap to be adhered to the skin of the penis (e.g., on the glans penis and/or the body of the penis). The adhesive strap may be made of a flexible material so that the adhesive strap may wrap around the penis thereby helping secure the incontinence device to the penis. In some embodiments, the adhesive strap may be attached to the concave receiver, providing adhesion attachment strength for the incontinence collection device. In some implementations, the adhesive strap may be included in the incontinence collection device in combination with the one or more adhesive flaps or tabs, providing further adhesion attachment strength for the incontinence device. In yet another embodiment, the adhesive strap may be included in the incontinence collection device in combination with the concave receiver and or the one or more adhesive flaps or tabs thereby providing further adhesion attachment strength for the incontinence device.

In some embodiments, the incontinence collection devices of the present invention include a collection valve that is in fluid communication with the collection conduit and receives urine therefrom. The collection valve may be a one way valve that prevents backflow into the collection conduit and the collection hole. The collection valve may be of various one-way internal valve designs. In some embodiments, the collection valve may have a double membrane structure, in which the distal ends of the membrane are intermittently bonded together, such that there are intermittent passages between the membranes at or near the distal ends thereof that allow urine to pass downstream from the collection hole through the collection valve, but the distal ends of the membrane are prevented from separating and allowing backflow. The passages between distal ends of the dual membranes have a width in the range of about 1 mm to about 5 mm (e.g., about 1.5 mm to about 4 mm, about 2 mm to about 3.5 mm, or any value or range of values therein) and the bonding points between the membranes may have widths in the range of about 1 mm to about 3 mm (e.g., about 2 mm, or any value or range of values therein). The width of the bonding points may define the interval between adjacent passages. The collection valve allows urine to pass at low pressure and flow into a second collection conduit at the distal end of the collection valve. The urine may seep through the plurality of passages into the second collection conduit.

In some embodiments, the incontinence collection device may not include a concave receiver. In such embodiments, the collection valve may include a collection conduit at its proximal end for receiving urine directly from the external urethral orifice, which may engage with a central adhesive pad, as described above. The central adhesive pad may have a collection hole (e.g., an elliptical hole) therein for receiving and engaging the collection conduit of the collection valve, which may be placed in direct contact with the glans penis in order to collect excreted urine. The collection conduit may be secured to the central adhesive pad by an adhesive or other fastening mechanism.

Once the urine passes through the collection valve and into the second collection conduit, the urine may pass into a collection receptacle which has a proximal receiving hole in fluid communication with the second collection conduit. The collection receptacle may have a volume sufficient to hold several hours of average urine excretion for an adult male. For example, the collection receptacle may have a maximum volume in a range of about 8 fluid oz. to about a quart. The collection receptacle may be made of a flexible material (e.g., rubber, polyurethane rubber, non-latex material such as nitrile, etc.) to allow the structure to collapse when empty or nearly empty, and to conform to the body as a person wearing the incontinence collection device moves.

The collection receptacle may include a one-way valve of various designs. In some embodiments, the one-way valve of the collection receptacle may have a similar structure to the one-way valve of the collection valve. In such embodiments, the collection valve may have a double membrane structure, in which the distal ends of the membrane are intermittently bonded together, such that there are intermittent passages between the membranes at or near the distal ends thereof that allow urine to pass downstream from the collection valve into the collection receptacle, but the distal ends of the membrane are prevented from separating and allowing backflow. The passages between distal ends of the dual membranes have a width in the range of about 1 mm to about 20 mm (e.g., about 5 mm to about 15 mm, about 8 mm to about 12 mm, or any value or range of values therein) and the bonding points between the membranes may have widths in the range of about 1 mm to about 20 mm (e.g., about 3 mm to about 18 mm, about 5 mm to about 15 mm, or any value or range of values therein). The width of the bonding points may define the interval between adjacent passages. The one-way valve of the collection receptacle allows urine to pass at low pressure (e.g., seep through the plurality of passages) and flow into the collection receptacle for storage. In some implementations, the dual membrane one-way valve may be connected along a lateral edge to the interior of the collection receptacle in order to aid in keeping the dual membrane structure in a flattened arrangement with the two membranes interfacing with one another in close proximity. The connection of the dual membranes to the interior of the collection receptacle may aid in preventing backflow of urine through the one-way valve to the collection valve.

In some implementations, the collection receptacle may have a structural features that allow the receptacle to expand with the flow of urine into the collection receptacle at relatively low pressures. For example, the collection receptacle may include billow-like structures or pleats at one or more points along the wall of the collection receptacle. Such billow-like structures or pleats may facilitate the collapse of the receptacle into a flat arrangement, such that the walls of receptacle are roughly parallel to the dual membrane one-way valve therein. The dual membranes of the one-way valve structure may be attached to the collection receptacle at or near the billow-like structure or pleats to further facilitate the collapsed, flat arrangement.

The collection receptacle may include a drainage conduit at its inferior, distal end for draining fluid from the collection receptacle. The drainage conduit may incorporate a drainage valve at the distal end. In some embodiments, the valve be of various designs that allow the user to open the drainage conduit without needing to have his hands near the distal opening of the drainage conduit. Thus, the drainage conduit may have a sufficient length to allow the drainage valve to be positioned sufficient distance upstream of the distal end of the drainage conduit, such that the collection receptacle can be drained without the user getting urine on his hands or spillage of the urine on the user or other undesirable places (e.g., the floor, user's pants, etc.). The drainage conduit may have a length in a range of about ¼ inch to about five inches (e.g., about a ¼ inch to about two inches, or any value or range of values therein).

The valve may be of various designs that are operable to be positioned in-line in the drainage conduit and upstream of the distal opening of the drainage conduit (e.g., butterfly valve, cross valve, pinch valve, etc.). The user may manually control the drainage valve in order to drain the urine from the collection receptacle into a desired location (e.g., a toilet). In some embodiments, the drainage valve is a pinch valve having a compressible bulb with a flexible actuator having a plug for mechanically blocking the distal end of the compressible bulb. The pinch valve may have closed condition (no pressure applied to the pinch valve by the user), in which the plug obstructs the distal end of the valve to prevent flow through the valve, and an open condition (user applies pressure to the pinch valve) in which the plug is proximally retracted from the end of the valve to allow flow through the valve. In some embodiments, the flexible actuator includes two or more (e.g., three, four, six, eight, etc.) resilient arms each having an outwardly protruding elbow that rests near or engages with the interior side of the wall of the compressible bulb. In some embodiments, the elbows may be mechanically attached to the interior of the compressible bulb to keep the resilient flexible frame in place within the compressible bulb. In other embodiments, the elbows may not be mechanically attached to the interior of the bulb. The flexible actuator may also include one or more central members connected to the resilient arms at or near a proximal end of the one or more central members and to the plug at the distal end of the one or more central members. The one or more central members may act as a piston that moves (1) proximally when the valve is pinched by the user, thereby retracting the plug away from the distal end of the valve, and (2) distally when the valve is released by the user, thereby inserting the plug into the distal end of the valve to obstruct passage of fluid through the valve. In operation, when the user engages the pinch valve (e.g., by compressing the bulb), the two or more resilient arms extend longitudinally, thereby moving the one or more central members proximally and retracting the plug and allowing urine to flow from the collection receptacle through the pinch valve. Upon release of the pinch valve, the two or more resilient arms resile to their original lengths and the central member(s) and the plug move distally and the plug seals the valve. It is to be understood that other valve structures operable to positioned in-line in the drainage conduit are encompassed within the scope of the present invention.

In some implementations, the drainage valve may detachable so that it may be replaced. In such implementations, the drainage valve may include a coupling mechanism that allows the valve to be attached and secured to the end of the drainage conduit, such as threading, interlocking ridges with the distal end of the drainage conduit, etc.

The incontinence collection devices of the present invention may also include a relief valve to allow gas (e.g., air) to pass into the incontinence collection device as urine flows out of the device. The relief valve may facilitate unimpeded flow of urine through the structures of the incontinence collection device (e.g., the collection receptacle, the drainage conduit, etc.) at low fluid pressure. The air relief valve may be positioned at various points on the incontinence collection devices of the present invention, including, but not limited to, the collection valve, the collection receptacle, etc.

Male external incontinence devices are typically attached to the glans penis. It is to be appreciated that such conditions as urostomy wherein an ureteroenteric anastomosis or ileal conduit urinary diversion is created so that one excretes urine in a different place than the glans penis. A urostomy is a surgical procedure that creates an artificial opening (typically called the stoma) for the urinary system. A urostomy procedure is performed on an individual where voiding of the bladder through the urethra is not possible (e.g., after extensive surgery, an obstruction, etc.), and urine excretion is rerouted through a stoma in the abdominal wall. The incontinence collection devices of the present invention may be used with a surgically created excretion points, such as a stoma, wherein urine is excreted. In such cases, embodiments of the incontinence collection device that include an adhesive pad for contacting the excretion point (e.g., rather than a concave receiver) may be used for attaching the incontinence collection device to the abdominal wall and engaging the receiving conduit with the stoma.

In one aspect, the present invention relates to an incontinence collection device that includes an attachment member having an adhesive on a surface of the attachment member and an exit hole for allowing the passage of urine, wherein the attachment member is operable to attach to a distal end of a penis; a collection member connected to the attachment member, the collection member comprising a collection conduit having a proximal end in fluid communication with the attachment member, a one-way internal valve in fluid communication with the collection conduit that is operable to prevent backflow of urine, and a distal conduit; a collection receptacle in fluid communication with the distal conduit of the collection member; and an air relief valve in fluid communication with the collection receptacle. The one-way valve includes a flexible dual membrane structure. The collection member may include a concave receiver operable to engage with the end of the penis, and may be conformable to the end of the penis and the concave receiver may have an adhesive on an interior thereof for adhering the concave receiver to the penis. The collection receptacle may include a second one-way valve for preventing backflow from the collection receptacle. The collection receptacle may have an exit conduit at a distal end thereof and a drainage valve. The drainage valve may be a pinch valve comprising a compressible bulb having a drainage hole in a distal end thereof; and a resilient, flexible valve mechanism comprising an actuator having at least two resilient arms having an elbow therein, the arms being in mechanical connection with an interior of the compressible bulb; a central member including a piston member having a proximal end that is mechanically connected to proximal ends of the resilient arms, and a distal end, a plug attached to the distal end of the bar, wherein the plug is operable to seal the drainage hole.

In another aspect, the present invention relates to an incontinence collection device that includes a collection member connected to an attachment member, the collection member comprising a collection conduit having a proximal end in fluid communication with a collection hole, a first one-way valve in fluid communication with the collection hole that is operable to prevent backflow of urine, and a distal conduit; a collection receptacle in fluid communication with the distal conduit of the collection member, the collection receptacle includes a second one-way valve for preventing backflow from the collection receptacle; and a drainage conduit in fluid communication with the collection receptacle operable to drain fluid from the collection receptacle. The collection member may include a concave receiver operable to engage with the end of the penis having a collection hole for alignment with the external urethral orifice of the penis and a raised bead surrounding the collection hole on the interior thereof, and the concave receiver is conformable to the end of the penis and the concave receiver has an adhesive on an interior thereof for adhering the concave receiver to the penis. The first one-way valve may include a flexible dual membranes that are connected together at their edges and have intermittent passages between the dual membranes at distal ends thereof. The incontinence collection device may include a drainage valve in fluid communication with the drainage conduit. The drainage valve may be a pinch valve comprising a compressible bulb having a drainage hole in a distal end thereof; and a resilient, flexible valve mechanism comprising an actuator having at least two resilient arms having an elbow therein, the arms being in mechanical connection with an interior of the compressible bulb; a central member including a piston member having a proximal end that is mechanically connected to proximal ends of the resilient arms, and a distal end, a plug attached to the distal end of the bar, wherein the plug is operable to seal the drainage hole.

In another aspect, the present invention relates to an incontinence collection device that includes a collection member connected to an attachment member, the collection member comprising a concave receiver operable to engage with an end of a penis having a collection hole for alignment with the external urethral orifice of the penis; a collection conduit having a proximal end in fluid communication with the collection hole, a one-way valve in fluid communication with the collection hole that is operable to prevent backflow of urine, and a distal conduit; a collection receptacle in fluid communication with the distal conduit of the collection member; and a drainage conduit in fluid communication with the collection receptacle operable to drain fluid from the collection receptacle. The incontinence collection device may include a drainage valve in fluid communication with the drainage conduit. The concave receiver may be conformable to the end of the penis and the concave receiver has an adhesive on an interior thereof for adhering the concave receiver to the penis. The one-way valve may include flexible dual membranes that are connected together at their edges and have intermittent passages between the flexible dual membranes at distal ends thereof. The collection receptacle may include a second one-way valve for preventing backflow from the collection receptacle. The drainage valve may be a pinch valve comprising a compressible bulb having an drainage hole in a distal end thereof; and a resilient, flexible valve mechanism comprising an actuator having at least two resilient arms having an elbow therein, the arms being in mechanical connection with an interior of the compressible bulb; a central member including a piston member having a proximal end that is mechanically connected to proximal ends of the at least two resilient arms, and a distal end, and a plug attached to the distal end of the bar, wherein the plug is operable to seal the drainage hole.

It is to be understood that both the general description and the following detailed description are exemplary and explanatory only and are not meant to limit the present invention. One with ordinary skill in the art will recognize that the general description and the detailed description will recognize that alterations and equivalents not described herein are captured in the spirit of the invention.

BRIEF DESCRIPTION OF THE DRAWINGS

FIG. 2D shows a side view of a urine collector according to some embodiments of the present invention.

FIG. 4A shows a frontal view of a collection receptacle with a drainage valve according to some embodiments of the present invention.

FIG. 7D shows a perspective view of an undergarment according to some embodiments of the present invention.

DETAILED DESCRIPTION OF THE EXEMPLARY EMBODIMENTS

Reference will now be made in detail to certain embodiments of the invention, examples of which are illustrated in the accompanying drawings. While the invention will be described in reference to these embodiments, it will be understood that they are not intended to limit the invention. To the contrary, the invention is intended to cover alternatives, modifications, and equivalents that are included within the spirit and scope of the invention as defined by the claims. In the following disclosure, specific details are given to provide a thorough understanding of the invention. However, it will be apparent to one skilled in the art that the present invention may be practiced without these specific details.

Figure 1A:
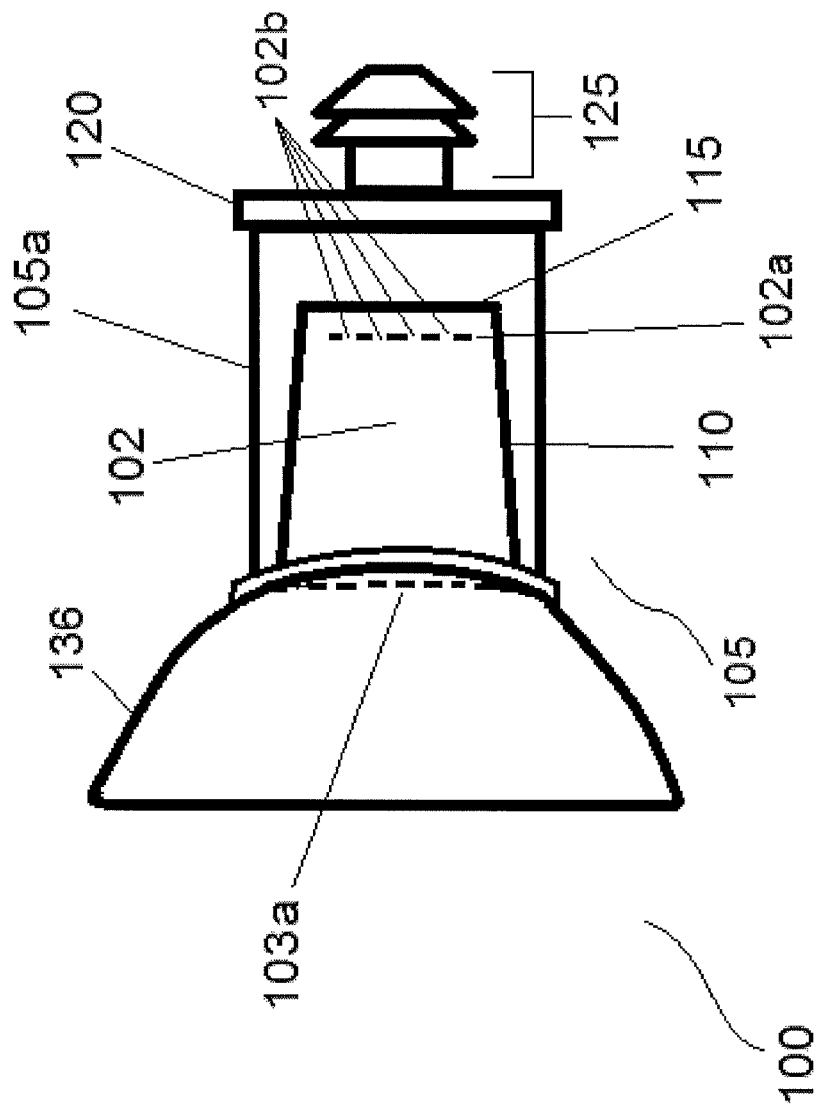
FIG. 1A shows a side view of a urine collector according to some embodiments of the present invention
Figure 1C:
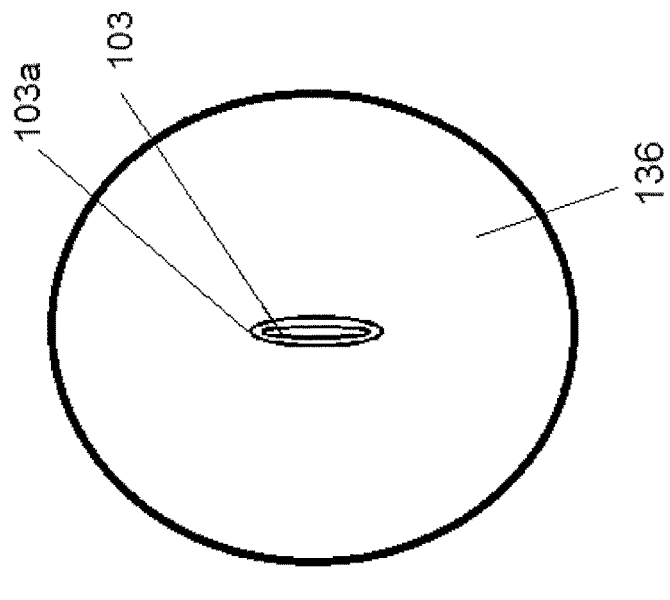
FIG. 1C shows a top view of a urine collector according to some embodiments of the present invention.
Figure 1B:
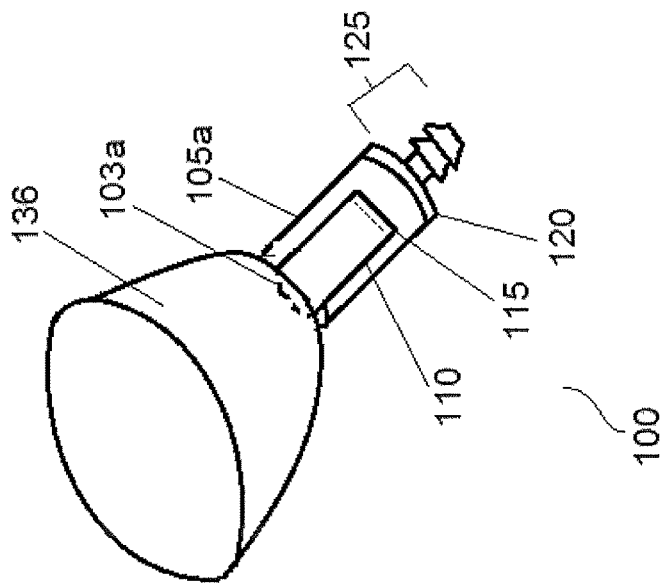
FIG. 1B shows a perspective view of a urine collector according to some embodiments of the present invention.

FIGS. 1A-D collectively show, without limitation, a collection member 100. Referring to FIGS. 1A-B, the collection member 100 is made up of a concave receiver 136 (e.g., a cup), a collection valve 105 having a proximal end in fluid connection with concave receiver 136, and distal collection conduit 120. The concave receiver 136 is a cup-like structure that is operable to be placed at the distal end of the penis (glans penis), and form-fit to the glans-penis to provide a relatively large surface area interaction between the concave receiver and the glans penis. The interior surface of the concave receiver 136 may have an adhesive thereon for adhering the concave receiver 136 to the glans penis. The adhesive may be a skin-safe adhesive such as hydrocolloid, acrylic, silicone, latex, or non-latex adhesive formulation. The cup-like structure may also aid in collecting excreted urine by providing a relatively large vessel for catching the excreted urine. The concave receiver 136 may include a collection hole 103 and a raised bead 103a that surrounds the collection hole 103. FIG. 1C shows the proximal surface of the concave receiver 136 that includes the raised bead 103a. The collection hole 103 may be aligned with external urethral orifice with the raised bead 103a surrounding the external urethral orifice to prevent leakage and direct urine flow through the collection member 105. The raised bead 103a may have adhesive for attaching and sealing the concave receiver to the glans penis to thereby securely align the collection hole 103 with the external urethral orifice.

The collection valve 105 includes a flexible, water-tight outer membrane wall 105a (e.g., a sleeve-like polymer structure) operable to allow urine to pass therethrough without leakage. The outer membrane wall 105a may have a water-tight connection at its proximal end with the concave receiver 136 and at its distal end with distal collection conduit 120. The collection valve 105 includes a one-way internal valve 110 that may be nested within the outer membrane wall 105a. The one-way internal valve 110 may have a flexible dual membrane structure 115 in which the lateral edges of the dual membranes are bonded to each other and the distal ends of the membranes are intermittently bonded together at bonding points 102a, such that there are intermittent passages 102b between the membranes at or near the distal ends thereof. This dual membrane structure 115 allows urine to pass downstream from the collection hole 103 through the one-way internal valve 110 without the distal ends of the membrane separating and allowing backflow. The passages 102b may have a width in the range of about 1 mm to about 5 mm (e.g., about 1.5 mm to about 4 mm, about 2 mm to about 3.5 mm, or any value or range of values therein) and the bonding points 102a may have widths in the range of about 1 mm to about 3 mm (e.g., about 2 mm, or any value or range of values therein). The width of the bonding points 102a may define the interval between adjacent passages 102b.

The one-way valve 110 may have a lumen 102 between the dual membranes that is maintained in a collapsed or nearly collapsed condition, such that urine can flow from the collection hole 103 into the proximal end of the dual membrane structure 115, but cannot backflow from the interior of the lumen collection valve 105 (the interior space of the outer membrane wall 105a that is external to the dual membrane structure 115) through the distal end of the dual membrane structure 115 because the bonding points 102a do not allow the distal ends of the dual membranes to separate. Thus, the distal end of the one way valve 110 may be prevented from opening by the bonding points 102a. The dual membrane structure 115 thereby allows liquid to pass through at a low pressure (e.g., pressure created by gravity flow of a small amount of liquid, urine, etc.), but prevents the backflow of urine toward the collection hole 103.

Figure 1D:
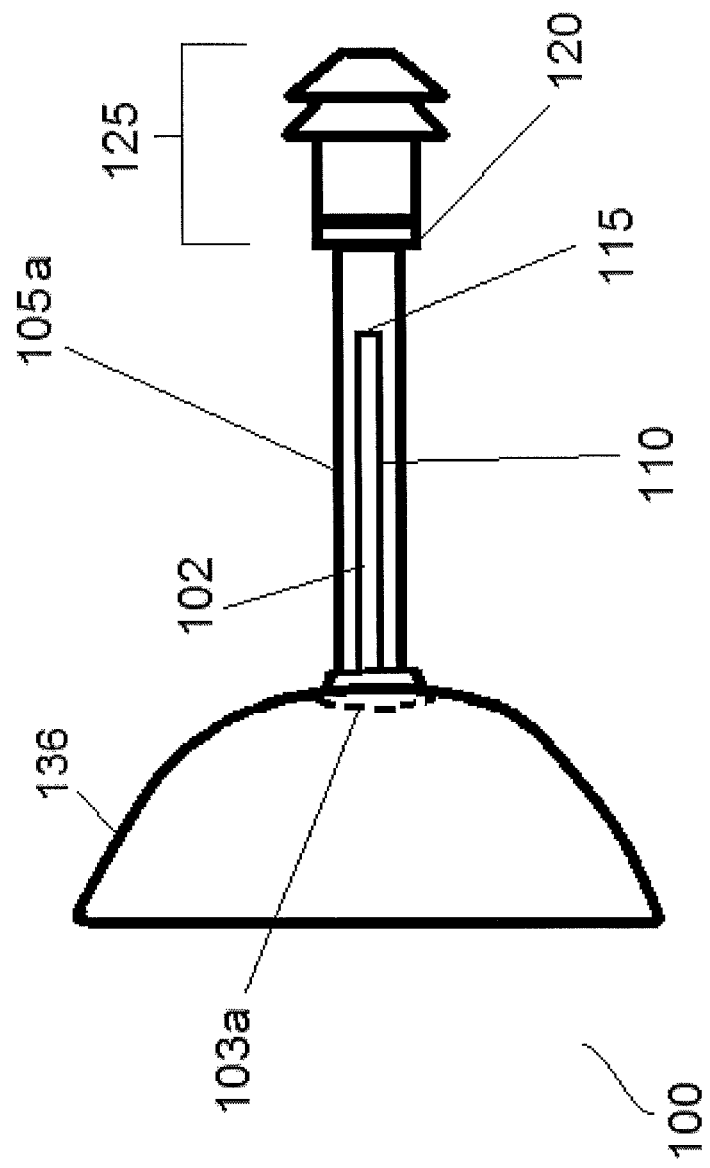
FIG. 1D shows a side view of a urine collector according to some embodiments of the present invention

The outer membrane wall 105a and the one-way internal valve 110 together form a collapsible substantially flat structure when urine is not passing through collection valve 105. FIG. 1D shows the collection member 100 which has been rotated 90°. The outer membrane wall 105a and the one-way internal valve 110 are shown as a flat structure in which there are potential spaces between the interfacing membranes through which urine can flow, when it is present.

Upon urine passing through the one-way valve 110 and into the collection conduit 105, the urine may be drained through the distal collection conduit 120. The distal collection conduit 120 may be a semi-rigid, semi-compressible, resilient structure capable of holding its shape. For example, it may be made of a various rubber materials, such as silicone rubber, polyurethane rubber, non-vulcanized natural rubber, polystyrene rubbers, polychloroprene, non-latex rubber materials, and other sturdy and (optionally) flexible materials. The distal collection conduit 120 may include a connector 125 having a connection mechanism for securely engaging with a collection receptacle. In the example shown in FIGS. 1A-1D, the connector 125 includes ridges at its distal end for engaging with the interior of a connection tube in the proximal end of a collection receptacle such that the distal collection conduit 120 may be securely placed in fluid communication with the collection receptacle. The ridges may serve to pressure fit and/or engage with complementary ridges within the connection tube of the collection receptacle. In other implementations, the connector 125 may have a different connection mechanism, such as threading or a quick-connect device. In still other implementations, the distal collection conduit 120 may be continuously and integrally formed with the collection receptacle.

Figure 2A:
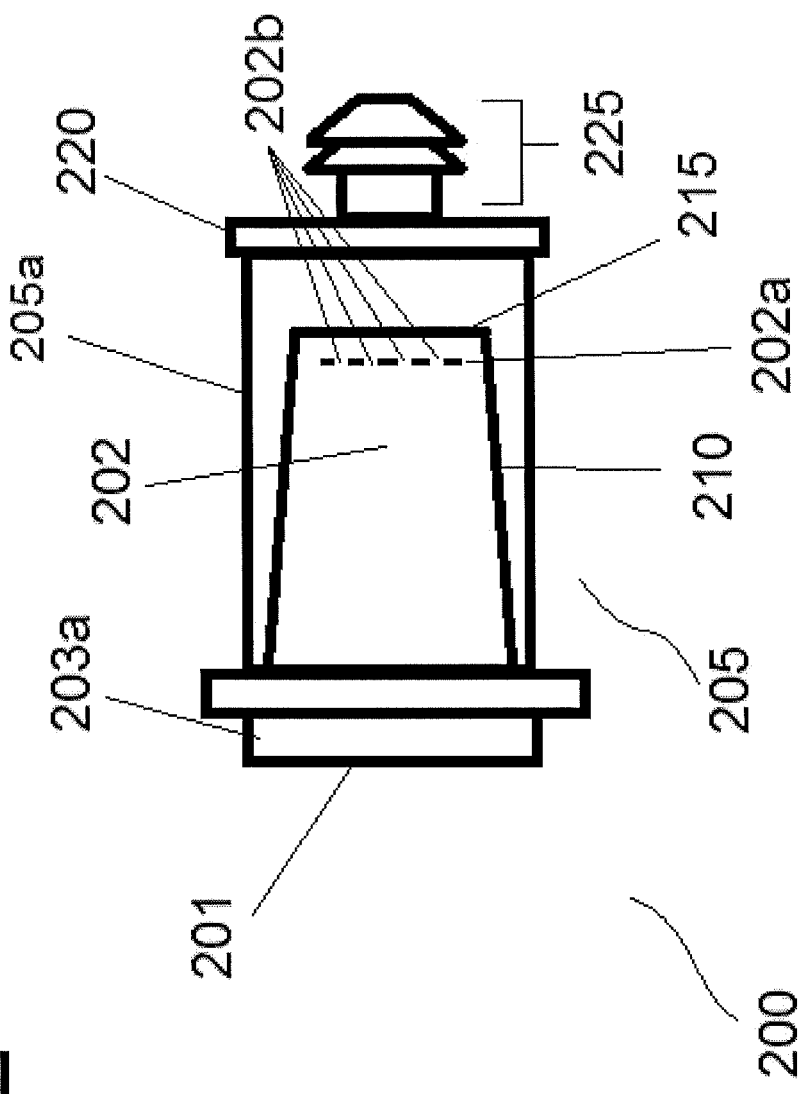
FIG. 2A shows an front view of the attachment device according to some embodiments of the present invention.
Figure 2C:
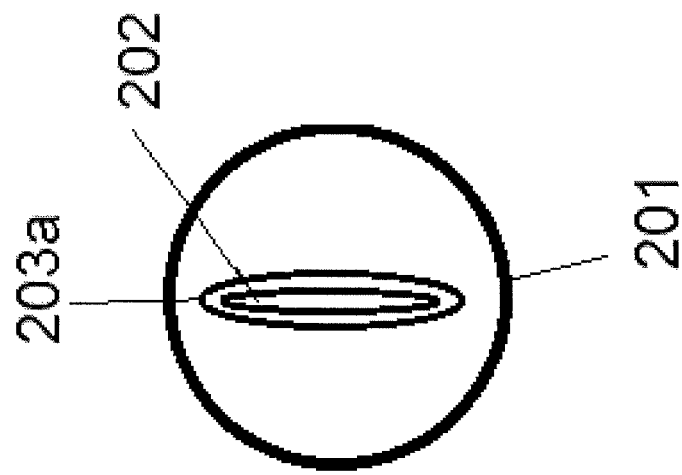
FIG. 2C shows a top view of a urine collector according to some embodiments of the present invention.
Figure 2B:
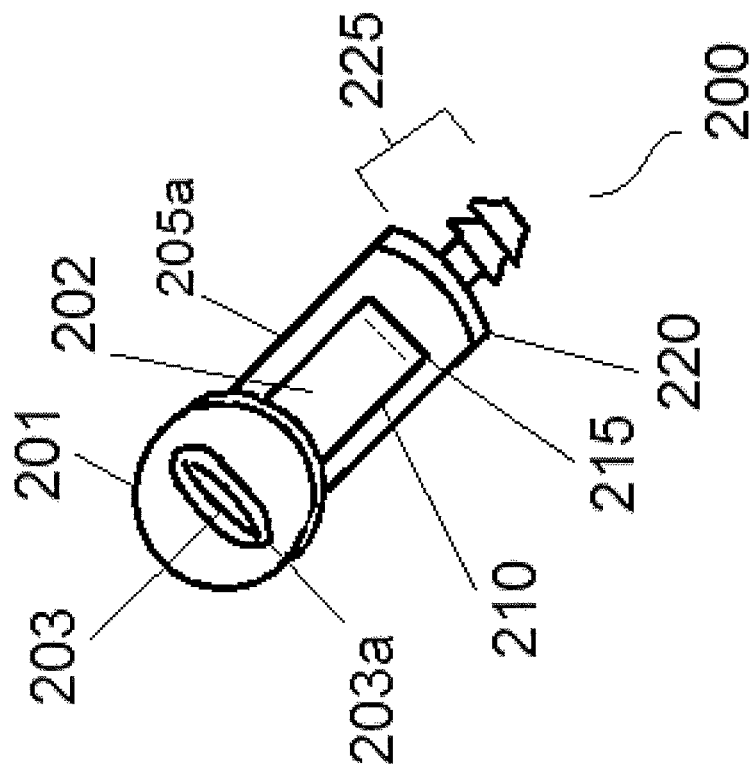
FIG. 2B shows a perspective view of a urine collector according to some embodiments of the present invention.

FIGS. 2A-D collectively show, without limitation, a collection member 200 that has some common features with the collection member 100 shown in FIGS. 1A-1D, but includes a different structure than the concave receiver 136. Referring to FIGS. 2A-B, the collection member 200 includes a collection disk 201, a collection valve 205 having a proximal end in fluid connection with collection disk 201, and collection conduit 220. The collection disk 201 is a circular structure (e.g., a flexible flat disk) that is made of a flexible and skin-safe material (e.g., silicone rubber, polyurethane rubber, non-vulcanized natural rubber, polystyrene rubbers, polychloroprene, non-latex rubber materials e.g., nitrile, and other appropriate materials) and is operable to be placed at the distal end of the penis (glans penis). The collection disk 201 may include a collection hole 203 and a raised bead 203a that surrounds the collection hole 203. FIGS. 2B-2C show the proximal surface of the collection disk 201 that includes the raised bead 203a. The collection hole 203 may be aligned with external urethral orifice with the raised bead 203a surrounding the external urethral orifice to prevent leakage and direct urine flow through the collection member 200. The collection hole 203 shown in FIGS. 2B-2C is elliptical, and it is to be understood that the collection hole 203 may alternatively have various shapes, including circular, polygonal, etc. The raised bead 203a may have adhesive for attaching and sealing the collection disk 201 to the glans penis to thereby securely align the collection hole 203 with the external urethral orifice.

The collection valve 205 has essentially the same structure as the collection valve 105 shown in FIGS. 1A-1D, except for the connection at its proximal end to collection disk 201, rather than a concave receiver. The outer membrane wall 205a (e.g., a sleeve-like polymer structure) may be flexible and water-tight and operable to allow urine to pass therethrough without leakage. The outer membrane wall 205a may have a water-tight connection at its proximal end with the collection disk 201 and at its distal end with distal collection conduit 220. The collection valve 205 includes a one-way internal valve 210 that may be nested within the outer membrane wall 205a, and may have the same construction as the one-way internal valve 105 described above. The one-way internal valve 210 may include a flexible dual membrane structure 215 in which the lateral edges of the dual membranes are bonded to each other and the distal ends of the membranes are intermittently bonded together at bonding points 202a, such that there are intermittent passages 202b between the membranes at or near the distal ends thereof. This dual membrane structure 215 allows urine to pass downstream from the collection hole 203 without the distal ends of the membrane separating and allowing backflow.

The one-way valve 210 may have a lumen 202 between the dual membranes that is maintained in a collapsed or nearly collapsed condition, such that urine flowing from the collection hole 203 into the proximal end of the dual membrane structure 215, but cannot backflow from the interior of the lumen collection valve 205 through the distal end of the dual membrane structure 215 because the bonding points 202a do not allow the distal ends of the dual membranes to separate.

The outer membrane wall 205a and the one-way internal valve 210 together form a collapsible substantially flat structure when urine is not passing through collection valve 205. FIG. 2D shows the collection member 200 which has been rotated 90°. The outer membrane wall 205a and the one-way internal valve 210 are shown as a flat structure in which there are potential spaces between the interfacing membranes through which urine can flow, when it is present.

The collection member 200 may further include a distal collection conduit 220, which may have the same construction as the distal collection conduit 120 described above. The distal collection conduit 220 may be a semi-rigid, compressible, resilient structure capable of holding its shape, and may include a connector 225 having a connection mechanism for securely engaging with a collection receptacle. In the example shown in FIGS. 2A-2D, the connector 225 includes ridges at its distal end for engaging with the interior of a connection tube in the proximal end of a collection receptacle such that the distal collection conduit 220 may be securely placed in fluid communication with the collection receptacle. The ridges may serve to pressure fit and/or engage with complementary ridges within the connection tube of the collection receptacle. In other implementations, the connector 225 may have a different connection mechanism, such as threading. In still other implementations, the distal collection conduit 220 may be continuously and integrally formed with the collection receptacle.

Figure 3A:
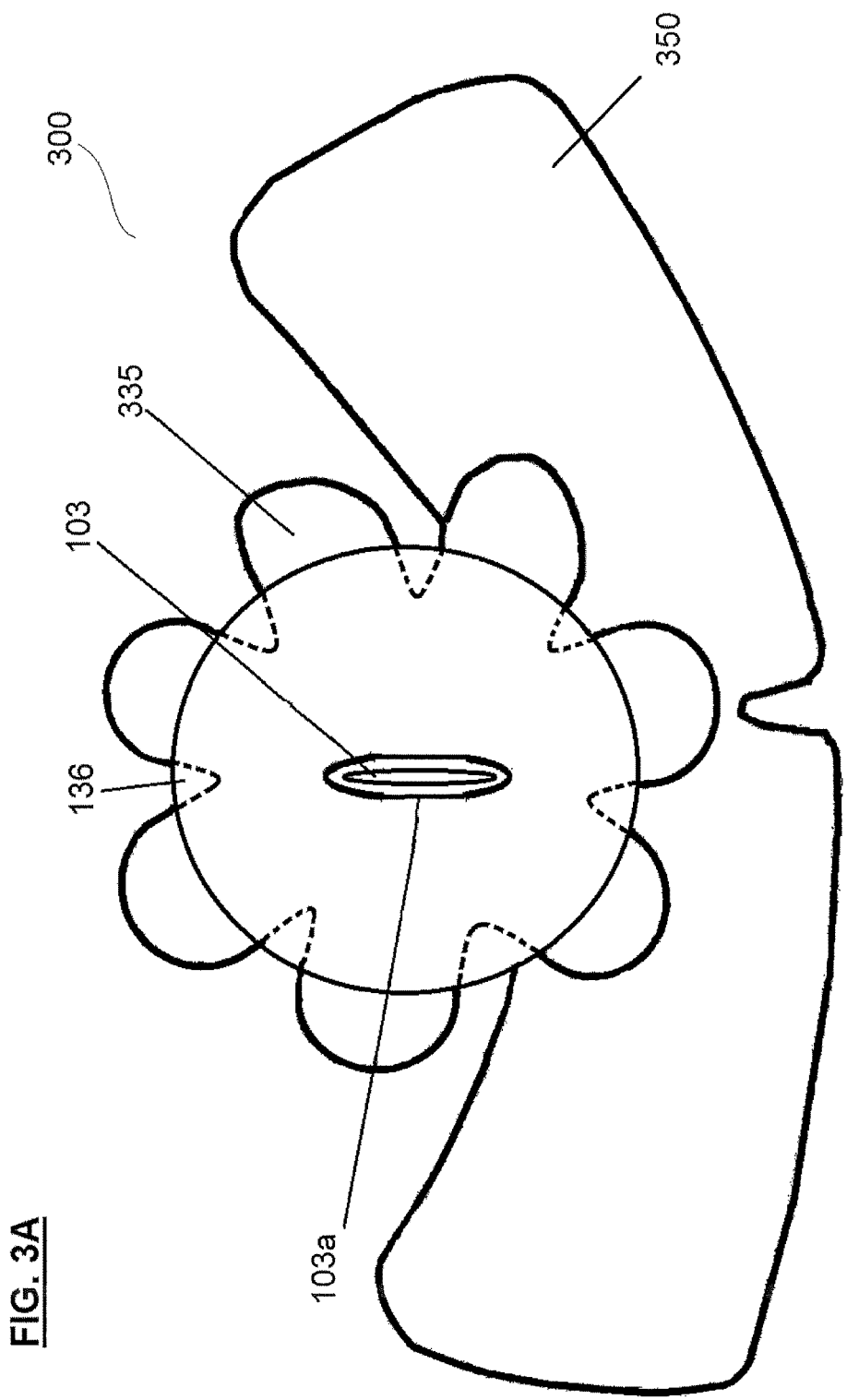
FIG. 3A shows a top view of an attachment device according to some embodiments of the present invention.
Figure 3B:
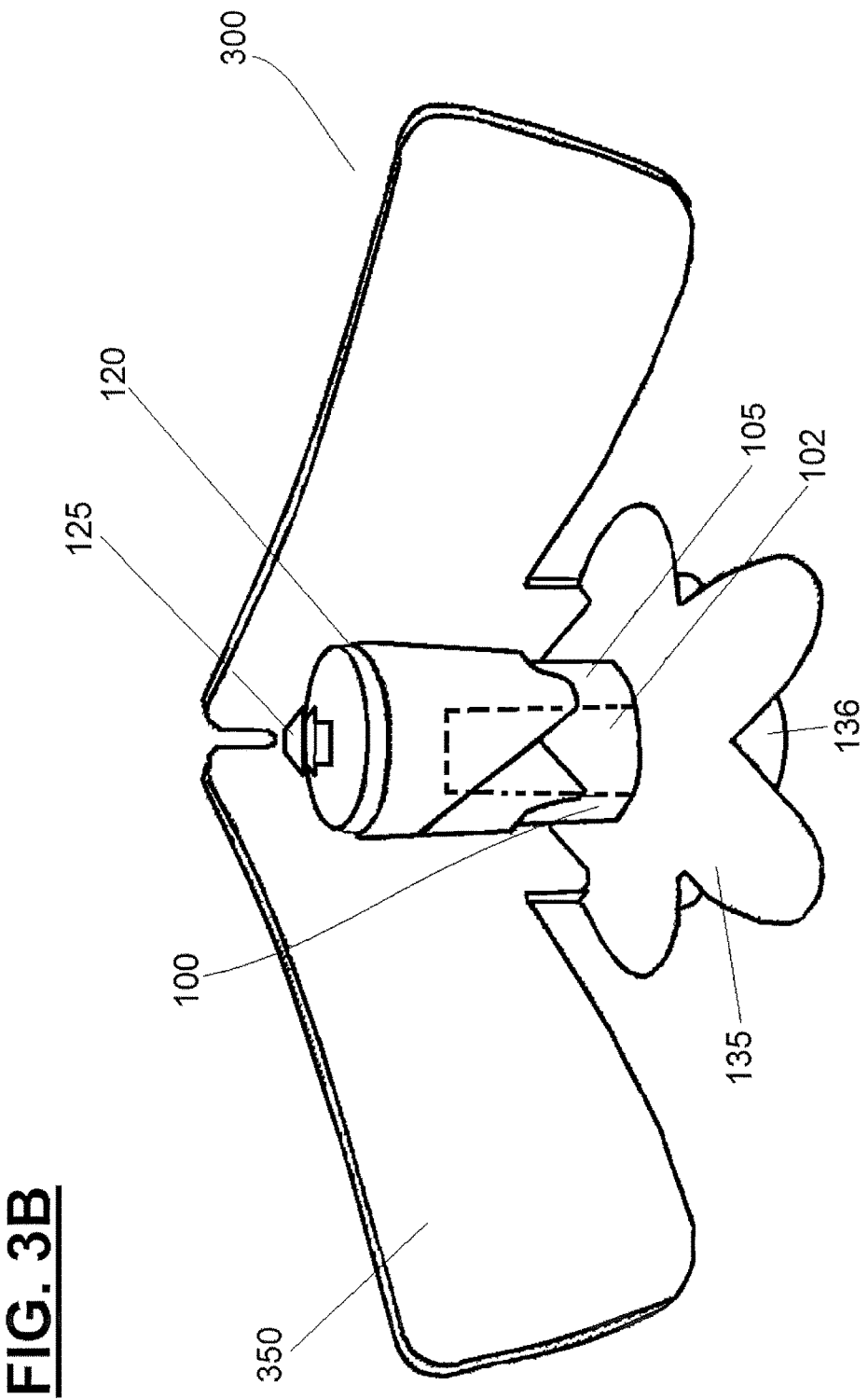
FIG. 3B shows an perspective view of an attachment device according to some embodiments of the present invention.

FIGS. 3A-3B illustrates, without limitation, an adhesive attachment member 300 which may be operable to be attached to the outer surface of the concave receiver 136 and may aid in attachment of the incontinence control device to the user. The adhesive attachment member 300 may have an adhesive on the upper surface thereof for adhering to both the outer surface of the concave receiver 136 and the skin of the user. The adhesive may be one that is skin-safe, such as such as a hydrocolloid, acrylic, silicone, latex, or non-latex adhesive formulation. In some embodiments, and without limitation, the adhesive attachment member 300 may have a central pad structure that contacts the outer wall of the concave receiver 136, and adhesive flaps 335 that extend from the central pad and beyond the edge of the concave receiver 136, such that they may be operable to adhere to the penis, when the concave receiver 136 is in contact with the glans penis. The adhesive flaps 335 may be pressed onto the penis on the glans penis and/or above the glans penis on the body of the penis.

The adhesive attachment member 300 may also include adhesive straps 350 to further aid in attaching the incontinence collection device to the penis. The adhesive straps 350 may be wrapped around the body of the penis when the concave receiver 136 is in contact with the glans penis. In some implementations, and without limitation, the straps 350 may be wrapped around the body of the penis after the concave receiver 136 has been adhered to the glans penis and the adhesive flaps 335 have been adhered to the penis. The combination of the concave receiver 136, the adhesive flaps 335 and the adhesive straps 350 provide for a secure attachment of the incontinence collection device to the penis.

Figure 5A:
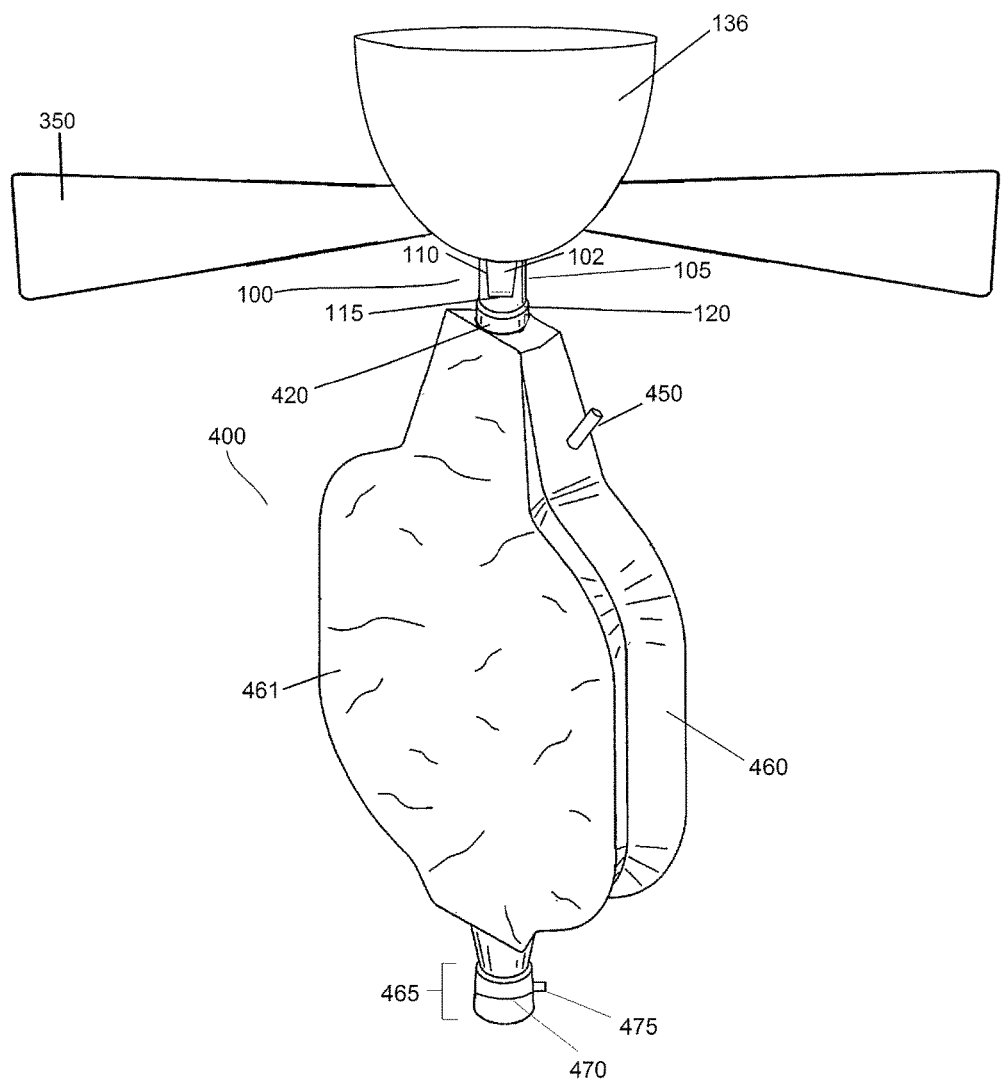
FIG. 5A shows a perspective view of an incontinence control device according to some embodiments of the present invention

In some embodiments, and without limitation, the adhesive attachment member 300 may simply include adhesive straps 350 attached to the concave receiver 136, as shown in FIG. 5A. The adhesive straps 350 may be wrapped around the body of the penis when the concave receiver 136 is in contact with the glans penis. In some implementations, and without limitation, the concave receiver 136 may include an adhesive on the inner surface thereof, and the adhesive straps 350 may be wrapped around the body of the penis after the concave receiver 136 has been adhered to the glans penis. The combination of the concave receiver 136 and the straps 350 may provide secure attachment of the incontinence collection device to the penis.

Figure 3C:
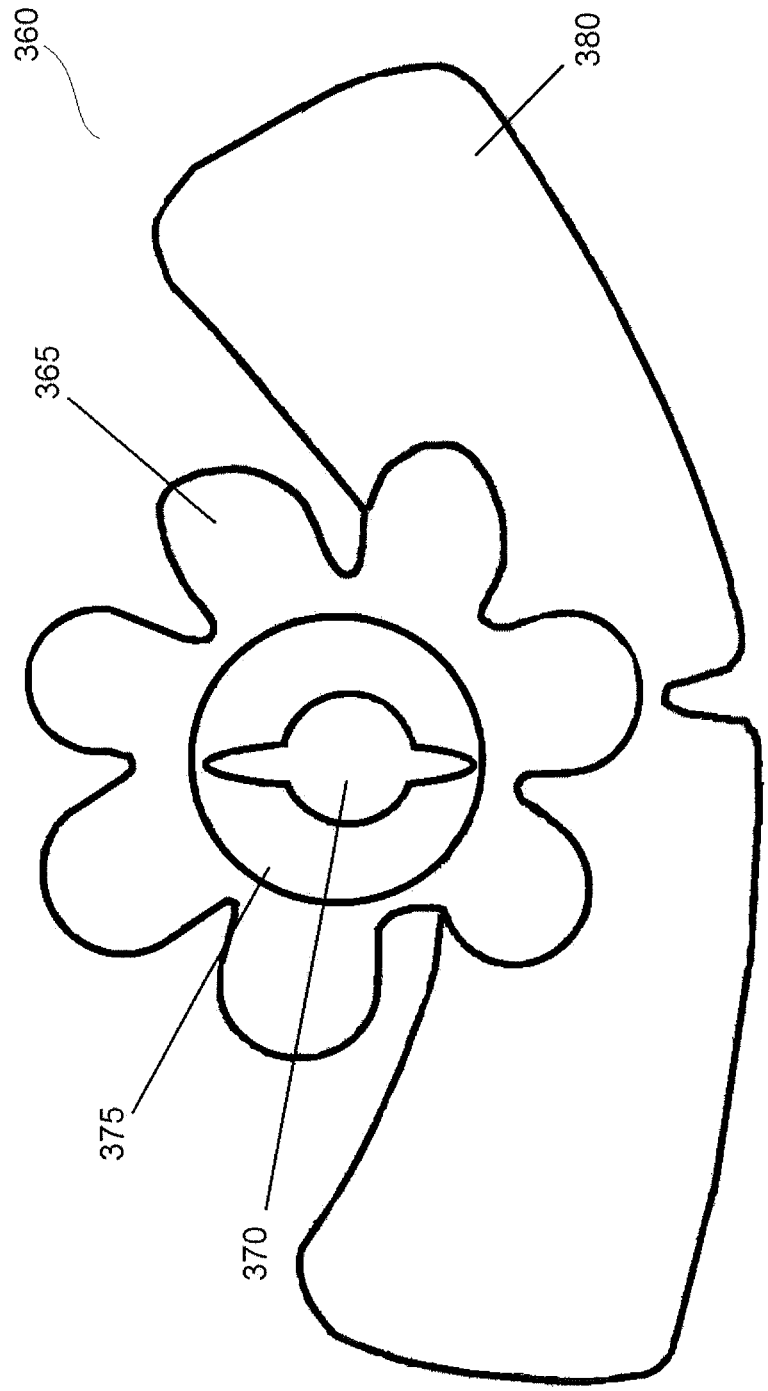
FIG. 3C shows a top view of an attachment device according to some embodiments of the present invention.

FIG. 3C shows an alternative embodiment of the adhesive attachment member. Adhesive attachment member 360 may be operable to be engaged with a collection member like collection member 200 that includes a collection disk 201. The collection member 200 may be positioned within receiving hole 370. For example, and without limitation, the distal collection conduit 220 and the collection valve 205 may be passed through the receiving hole 370 such that the collection disk 201 is positioned over an adhesive area 375, and the collection disk 201 may be secured in position over the receiving hole 370. Subsequently, the collection disk 201 and the adhesive flaps 365 and adhesive straps 380 may be adhered to the penis to secure the incontinence control device to the user. It is to be understood that the adhesive area 375 may simply be an area of equivalent size to the collection disk 201 on the adhesive attachment member 360, and that the entire surface of the adhesive attachment member 360 shown in FIG. 3C (including the adhesive flaps 365 and the straps 380) may have an adhesive thereon.

FIG. 4A shows collection receptacle 400 for receiving urine from the collection member (e.g., 100) and storing the urine until the user of the incontinence collection device drains the urine from the collection receptacle 400. The collection receptacle 400 may be a flexible, expandable bladder-like structure that receives and collects urine from the collection member (e.g., 100). The collection receptacle 400 may have a volume sufficient to hold several hours of average urine excretion for an adult male. For example, the collection receptacle 400 may have a maximum volume in a range of about 8 fluid oz. to about a quart. The collection receptacle 400 may be made of a flexible material (e.g., rubber, polyurethane rubber, non-latex material such as nitrile, etc.) to allow the structure to collapse when empty or nearly empty, and to conform to the body as a person wearing the incontinence collection device moves. The collection receptacle 400 may have a structural features that allow the receptacle to expand with the flow of urine into the collection receptacle at relatively low pressures. For example, the collection receptacle may include billow-like structures at one or more points along the wall of the collection receptacle. Such billow-like structures or pleats may facilitate the collapse of the receptacle into a flat arrangement. As shown in FIG. 4A, collection receptacle 400 may have an expandable pleated side 460 (pleated side 460 is best illustrated in FIG. 5A).

The collection receptacle 400 may be detachably or integrally connected to the collection member. In some embodiments, the collection receptacle may be attached to the collection member indirectly, for example, by a length of tubing. As shown in FIG. 4A, the collection receptacle may be connected to a collection member (e.g., collection member 100) by engagement of the distal connector 125 of collection member 100 with a connector 420. Connector 420 may be a tube having engagement structures that are complementary to an engagement mechanism of the distal connector 125. For example, the distal connector 125 may include circumferential ridges at its distal end for engaging with the interior of connector 420, which may include internal ribbing for engaging the ridges of connector 125 such that the distal conduit 120 may be securely placed in fluid communication with the collection receptacle 400. The ridges may serve to pressure fit and engage the ribbing within the connector 420. In other implementations, the connector 125 and the connector 420 may share a different connection mechanism, such as a quick connect device or complementary threading. In still other implementations, the distal collection conduit 120 may be continuously and integrally formed with the collection receptacle 400. The connection between the collection member 100 and the collection receptacle 400 allows urine to pass from the collection member 100 into collection receptacle 400.

The collection receptacle 400 may include a one-way valve of various designs. In some embodiments, the collection receptacle 400 may include a one-way valve 410 that may be nested within the outer walls of the collection receptacle. The one-way valve 410 may be similar in structure to the one-way valve of the collection member (e.g., one-way valve 110). The one-way internal valve 410 may have a flexible dual membrane structure 415 in which the lateral edges of the dual membranes are bonded to each other and the distal ends of the membranes are intermittently bonded together at bonding points 402a, such that there are intermittent passages 402b between the membranes at or near the distal ends thereof. The one-way valve 410 may have a lumen 402 between the dual membranes that is maintained in a collapsed or nearly collapsed condition. This dual membrane structure 415 allows urine to pass downstream from the connector 420 through the one-way valve 410 without the distal ends of the membrane separating and allowing backflow. The passages 402b may have a width in the range of about 1 mm to about 20 mm (e.g., about 5 mm to about 15 mm, about 8 mm to about 12 mm, or any value or range of values therein) and the bonding points 402a between the membranes may have widths in the range of about 1 mm to about 20 mm (e.g., about 3 mm to about 18 mm, about 5 mm to about 15 mm, or any value or range of values therein). The width of the bonding points 402a may define the interval between adjacent passages. The one-way valve 410 of the collection receptacle 400 allows urine to pass at low pressure (e.g., seep through the plurality of passages 402b) and flow into the outer lumen 461 of the collection receptacle 400 for storage. In some implementations, the dual membrane one-way valve 410 may be connected along its lateral edges to the interior of the collection receptacle 400 in order to aid in keeping the dual membrane structure 415 in a flattened arrangement with the two membranes of the dual membrane structure 415 interfacing with one another in close proximity. The connection of the dual membranes to the interior of the collection receptacle 400 may aid in preventing backflow of urine through the one-way valve 410 to the collection member.

The collection receptacle 400 may include a drainage valve 465 at its distal end that may be manually operated by the user. To aid in the flow of urine when the drainage valve 465 is in an open condition, the collection receptacle 400 may also include an air relief valve 450 positioned in the outer wall of the collection receptacle 400. The air relief valve 450 may aid in draining the urine from the collection receptacle 450 by allowing air to flow into the collection receptacle 400 as the urine is drained through the drainage 465 valve and thereby preventing the creation of a vacuum within the collection receptacle 400. As shown in FIG. 4A, the collection receptacle 400 includes an air relief valve 450 through which air may be drawn as urine is drained from the collection receptacle through the drainage valve. It is to be appreciated that the air relief 450 may include a liquid-proof valve (not shown) that prevents urine from being released from air relief valve 450.

Figure 4B:
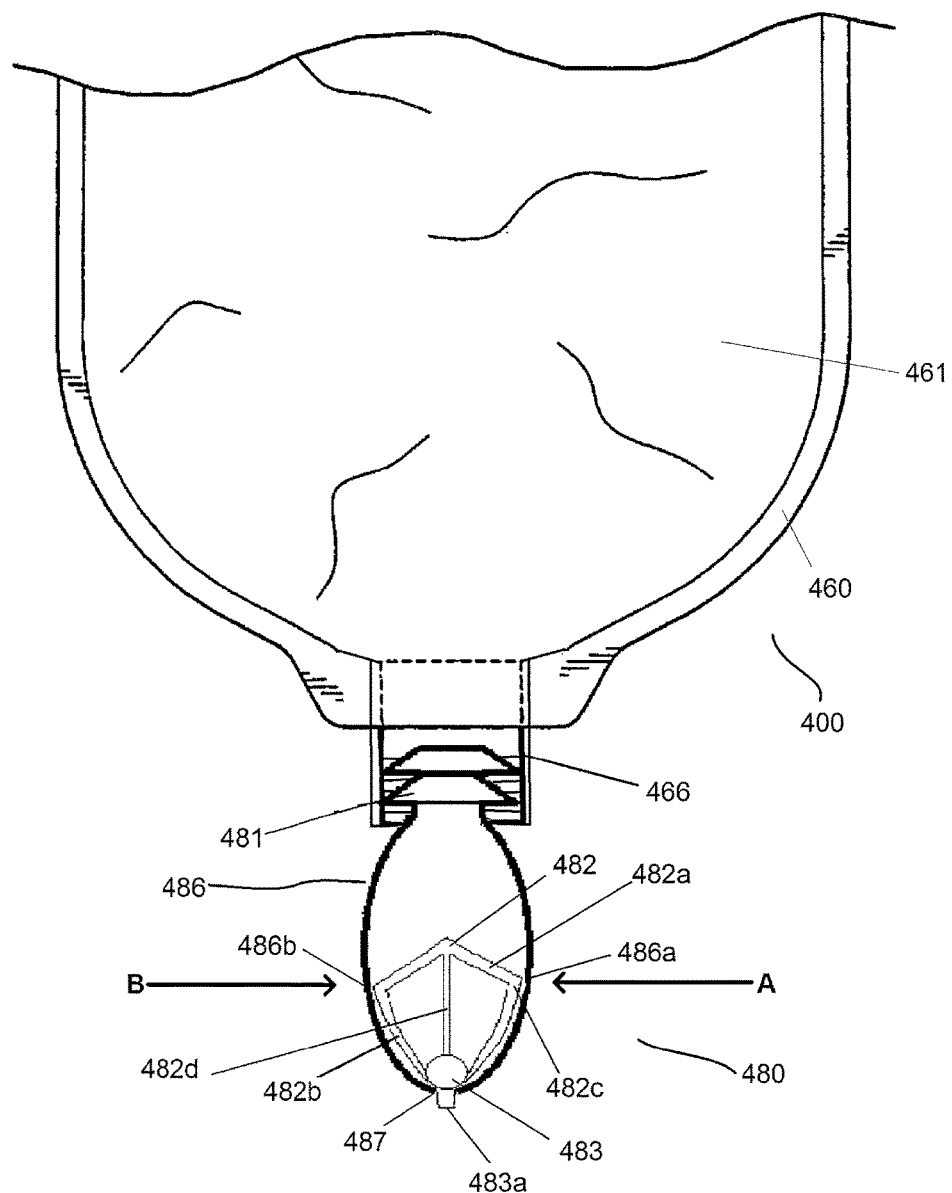
FIG. 4B shows a frontal view of a collection receptacle with a drainage valve according to some embodiments of the present invention.

FIGS. 4A-4E show exemplary embodiments of a drainage valve 465 for the incontinence collection device of the present invention. For example, FIG. 4A shows a drainage valve 465 that may include a drainage conduit 466 to collect urine at the distal end of collection chamber 400, a valve mechanism 470, and a valve actuator 475 for opening the valve mechanism 470. The drainage conduit 466 may be a rigid or semi-rigid polymer structure, such as a resilient flexible rubber structure that can maintain its shape, but may allow limited bending and manipulation (e.g., rubber, vulcanized rubber, etc.). Urine may flow by gravity to the distal end of the collection receptacle 400 and through the valve mechanism 470, when the user engages the valve actuator 475. In the example shown in FIG. 4A, the valve mechanism is a biased cross valve, that is biased to a closed position, and the user must push in the valve actuator 475 (a push button) in order to open the valve. Cross valve 470 has an opening (not shown) that aligns with the lumen of the drainage conduit when cross valve is pushed in, allowing urine to drain from the collection receptacle 400. The collection receptacles of the present invention may alternatively include other kinds of valve structures. Some alternative valve structures are discussed below.

Figure 4C:
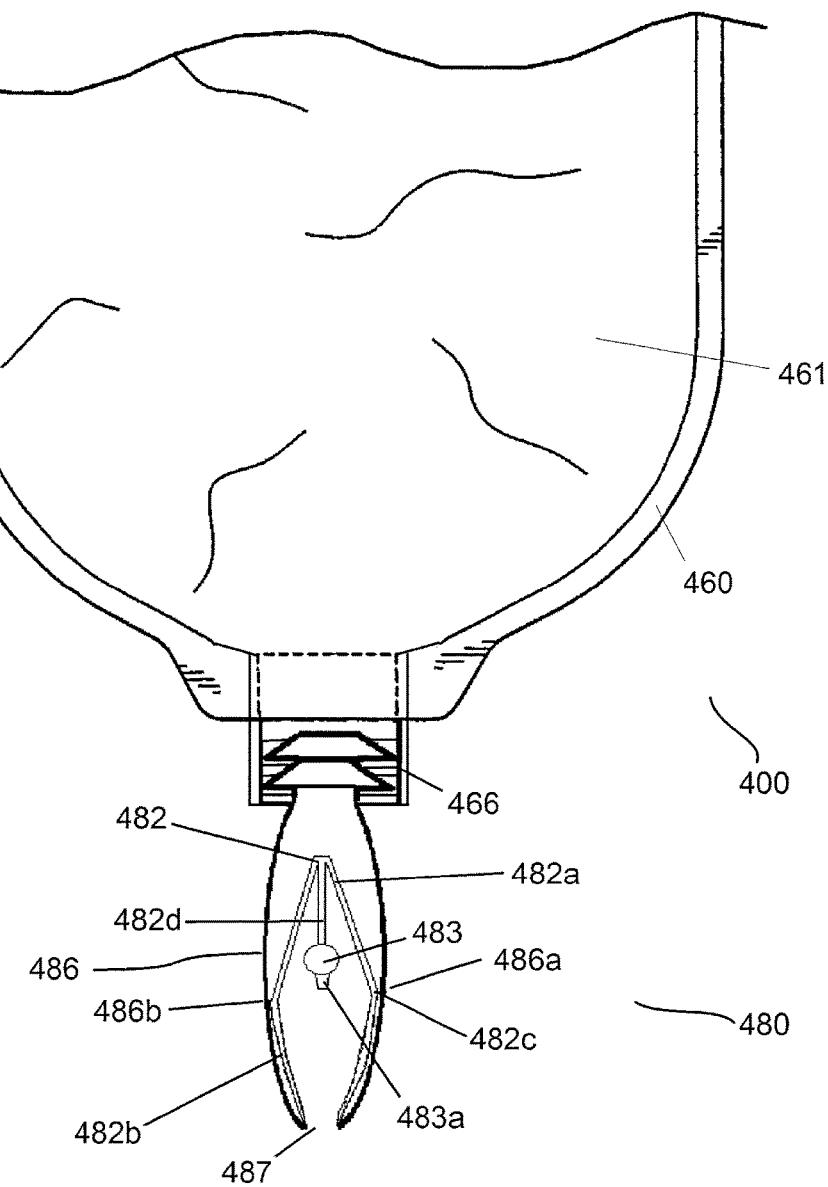
FIG. 4C shows a frontal view of a collection receptacle with a drainage valve according to some embodiments of the present invention.
Figure 4D:
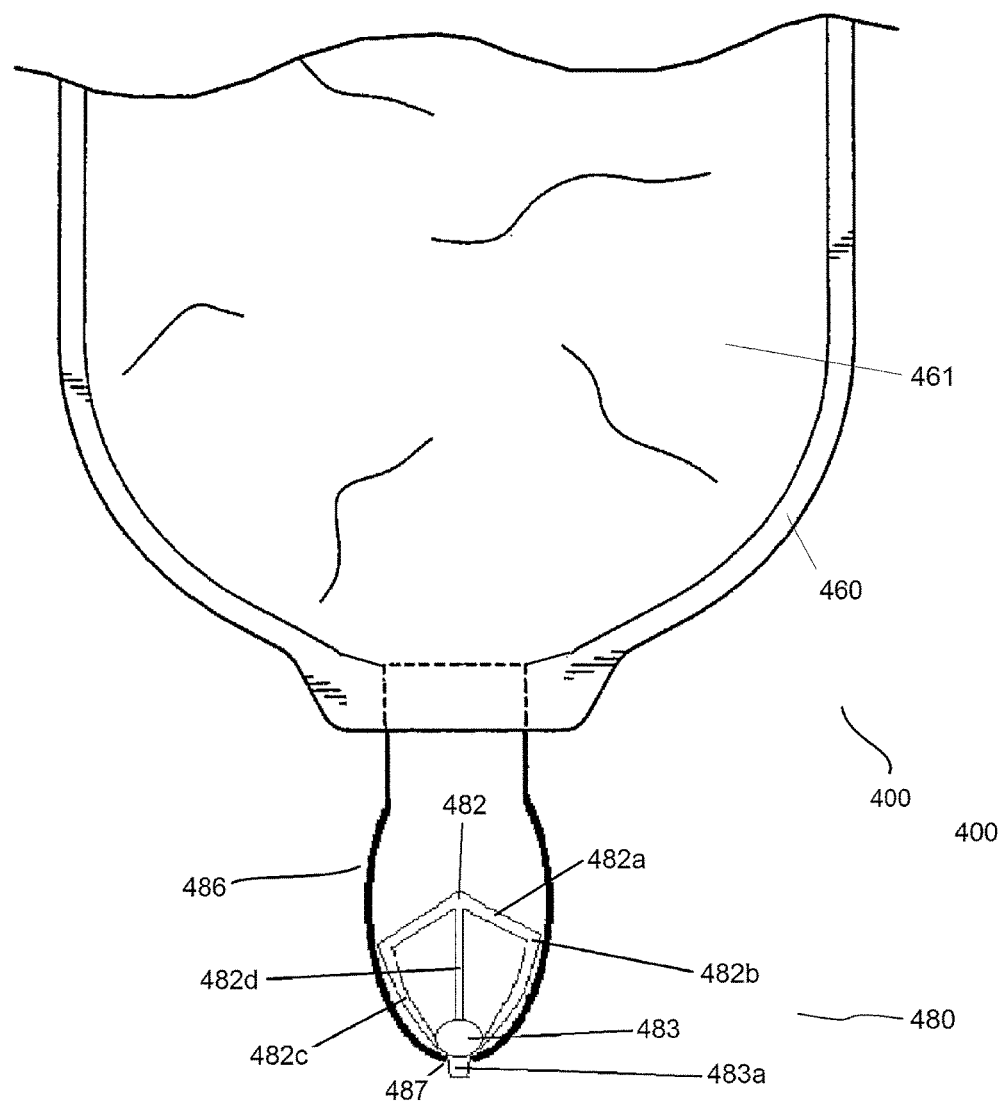
FIG. 4D shows a frontal view of a collection receptacle with a drainage valve according to some embodiments of the present invention.

FIGS. 4B-4E illustrate other embodiments of the drainage valve for the incontinence collection device of the present invention. It is to be understood that the following exemplary drainage valves would be a substitute for the drainage valve 465 shown in FIG. 4A, and would be engaged with the drainage conduit 466 or integrally formed with the distal end of the collection receptacle 400. FIGS. 4B-4D shows an embodiment of the drainage valve having a pinch valve structure. The pinch valve 480 comprises a compressible bulb 486, an actuator 482 that includes at least two (e.g., two, three, four, six, etc.) resilient arms 482a and 482b that project inferiorly within the compressible bulb 486. The at least two resilient arms 482a and 482b each have elbows 482c which engage with the interior of the compressible bulb 486 at points 486a and 486b. The at least two resilient arms 482a and 482b may be mechanically attached to the compressible bulb 486 such that the actuator 482 kept in position within the compressible bulb 486. The actuator 482 also has a central piston member 482d including at least one bar connected to a plug 483. The plug 483 may have a shape that is operable to engage and obstruct a tapered distal hole 487 at the distal end of the compressible bulb 486, to thereby prevent any fluid from flowing from the distal hole 487. The plug 483 may include a distal peg 483a at its distal end that has a complementary shape to a distal hole 487 of the compressible bulb 486.

The function of the actuator 482 is to prevent urine from being released from the collection receptacle 400 until the user pinches the pinch valve 480. Upon pinching at or near points 486a and 486b of compressible bulb 486 (e.g., according to arrows A and B), the elbows 482a and 482b are squeezed and elongated within the pinch valve 480. As the elbows 482a and 482b are squeezed and elongated, the angle between the upper and lower portions of each arm increases and the angles between the arms and the central piston member 482d decrease, and the central piston member 482d is retracted from the distal hole 487 of the compressible bulb 486. FIG. 4C shows the compressed condition of the compressible bulb 486 and actuator 482 when the user pinches the compressible bulb 486. In the compressed condition, the plug 483 is removed from the distal hole 487, thereby allowing urine to flow from the collection receptacle 400.

As previously mentioned, the actuator 482 is a resilient structure that resiles to its original shape once the user releases the compressible bulb 486, thereby returning the plug 483 and peg 483a into original position to obstruct the distal hole 487 of the compressible bulb 486. The actuator 482 may maintain its position within the compressible bulb 486 and thereby allow the plug 483 to return to its original position by the mechanical connection between the elbows 482c and points 486a and 486b within the compressible bulb.

The pinch valve 480 as shown in FIGS. 4B-4C is detachable from the collection receptacle 400, having ridges that may serve to pressure fit and/or engage with complementary ridges within the distal conduit of the collection receptacle 400. In other implementations, the pinch valve 480 may have a different connection mechanism, such as threading. In still other implementations, the pinch valve 480 may be continuously and integrally formed with the collection receptacle 400. As shown in FIG. 4D shows a pinch valve 480 wherein the pinch valve 480 is integrally formed with the distal conduit of the collection receptacle 400.

Variations in the pinch valve 480 structure shown in FIGS. 4B-4D are within the scope of the present invention. In some embodiments of the present invention, e.g., the actuator 482 may include more than 2 resilient arms (e.g., 3, 4, 5, 6, or more) that may radiate from the central piston member 482d in a symmetrical pattern. With additional arms, the user may be able to squeeze the compressible bulb 486 between any two diametric or about diametric points on the circumference of the compressible bulb 486 and compress the actuator 482. In some embodiments, and without limitation, the resilient arms (e.g., 482a and 482b) may have various designs, including broader arms to increase the surface area of the interface between the resilient arms and the interior of the compressible bulb 486, resilient arms that terminate at the contact between the arms and the bulb (the "elbows"), and various other designs. Additionally, in some embodiments, the plug 483 may have other shapes such as a conical shape that tapers at the distal end, an ellipsoid shape, etc. In some embodiments, the plug 483 may also include a hydrophobic outer material or coating (e.g., hydrophobic polyol, polyether polyol, amine-initiated polyol, carbodiimide-modified MDI, polymeric MDI, etc.) to aid in preventing urine from passing through the distal hole 487 of the compressible bulb 486 until it is compressed.

Figure 4E:
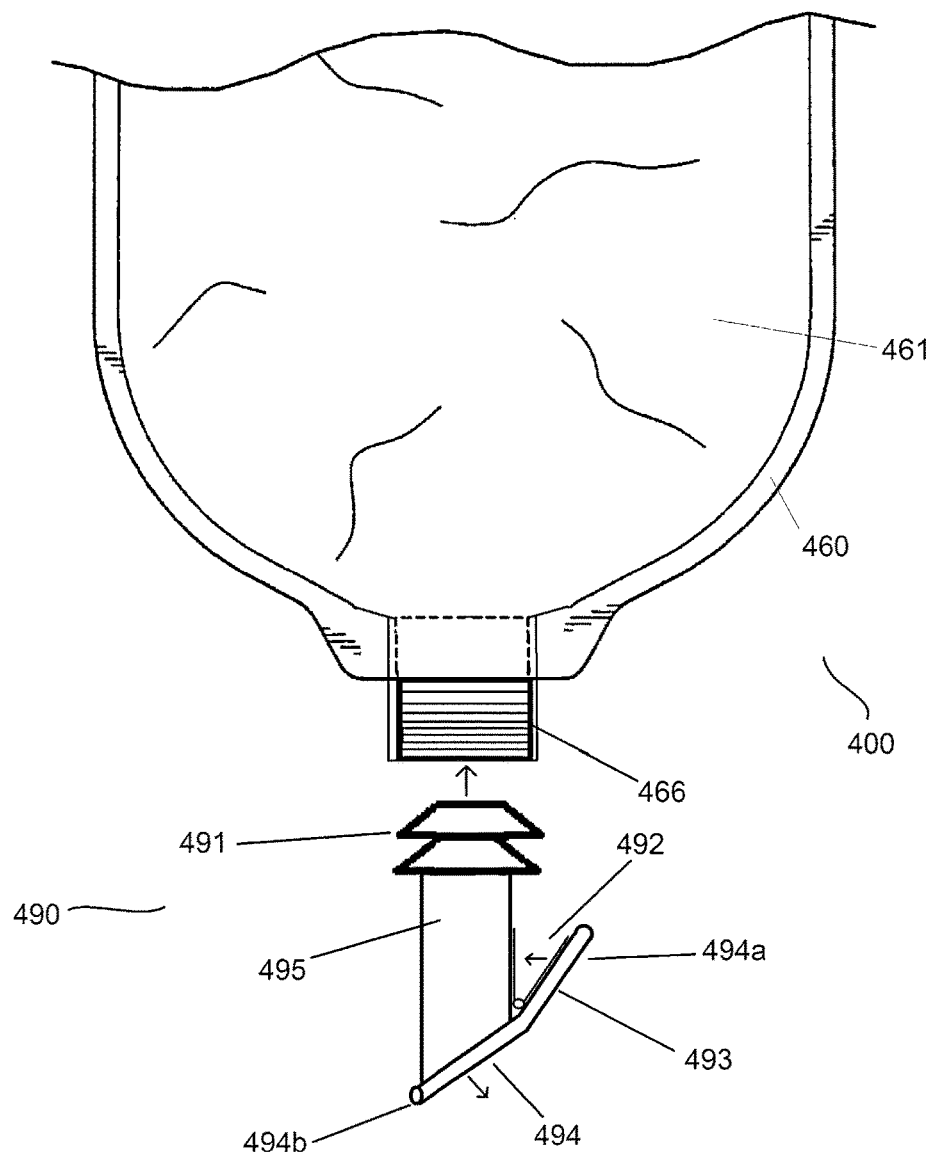
FIG. 4E shows a frontal view of a collection receptacle with a drainage valve according to some embodiments of the present invention.

FIG. 4E shows a further exemplary embodiment of the drainage valve 490 having a biased door 494 for covering the distal drainage hole of the collection receptacle. The drainage valve 490 includes a connector 491 for engaging and securing to the distal drainage conduit of the collection receptacle 400, a length of tube 495, and a sealing member 493. The sealing member 493 includes a spring-biased joint 492 that is fixedly attached to the tube 495, and a door 494 that is fixedly attached to the spring-biased joint 492. The door 494 may include a lever portion 494a that the user can press to reduce the angle between the lever portion 494a and the tube 495, and thereby open the drainage valve 490. Spring-biased joint 492 prevents the door 494 from opening without the user pressing the lever portion 494a. The perimeter of the door 494 may have a flexible, compressible O-ring or lip (e.g., made from rubber, vulcanized rubber, polyurethane, etc.) 494a to prevent urine from leaking through the drainage valve 490. In some embodiments, the door 494 may also include a hydrophobic outer layer or coating (e.g., hydrophobic polyol, polyether polyol, amine-initiated polyol, carbodiimide-modified MDI, polymeric MDI, etc.) on the area of the door 494 that engages with the distal rim of the tubing 495 to aid in preventing urine from leaking from the drainage valve 490. The drainage valve 490 may be attached to the distal drainage conduit 466 of the collection receptacle 400 by ridges that may serve to pressure fit and/or engage with complementary ridges within the distal conduit of the collection receptacle 400. In other implementations, the drainage valve 490 may have a different connection mechanism, such as threading. In still other implementations, the drainage valve 490 may be continuously and integrally formed with the collection receptacle 400.

FIGS. 5A-5D illustrate exemplary embodiments of the incontinence collection device of the present invention in full assembly, including a collection receptacle 400 in fluid connection with the distal collection conduit 120 of the collection member 100. FIG. 5A shows an exemplary embodiment in which collection member 100 is attached to collection receptacle 400 via the coupling of connector 125 to connector 420. In this embodiment, the incontinence collection device is attached to the penis by the concave receiver 136 and the adhesive straps 350. The concave receiver 136 may have an adhesive on the interior thereof and, in combination with the adhesive straps 350, may have sufficient adhesive to provide an adequately strong and reliable connection with the glans penis. In other implementations, the concave receiver 136 may only include adhesive on the raised bead 103a, and the adhesive straps 350 may provide most of the strength of attachment between the incontinence collection device and the penis. Additionally, the incontinence collection device shown in FIG. 5A may be further supported by an undergarment into which the incontinence collection device may be inserted during use. Such undergarments are discussed herein below.

Figure 5B:
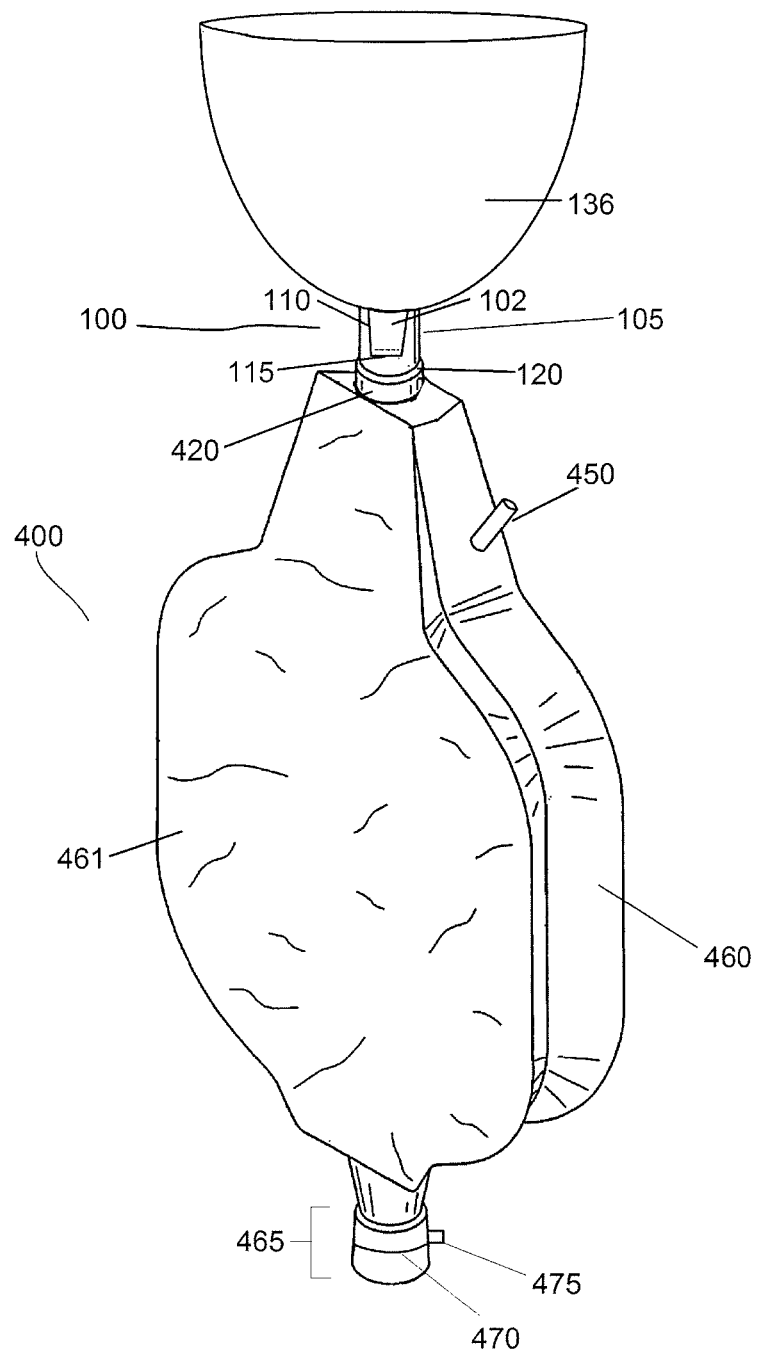
FIG. 5B shows a perspective view of an incontinence control device according to some embodiments of the present invention.

FIG. 5B shows an embodiment in which the adhesive attachment structure (e.g., adhesive straps 350) is not included because the concave receiver 136 may have sufficient adhesive in the interior thereof to provide an adequately strong and reliable connection with the glans penis. Additionally, the incontinence collection device shown in FIG. 5B may be further supported by an undergarment into which the incontinence collection device may be inserted during use. Such undergarments are discussed herein below.

Figure 5C:
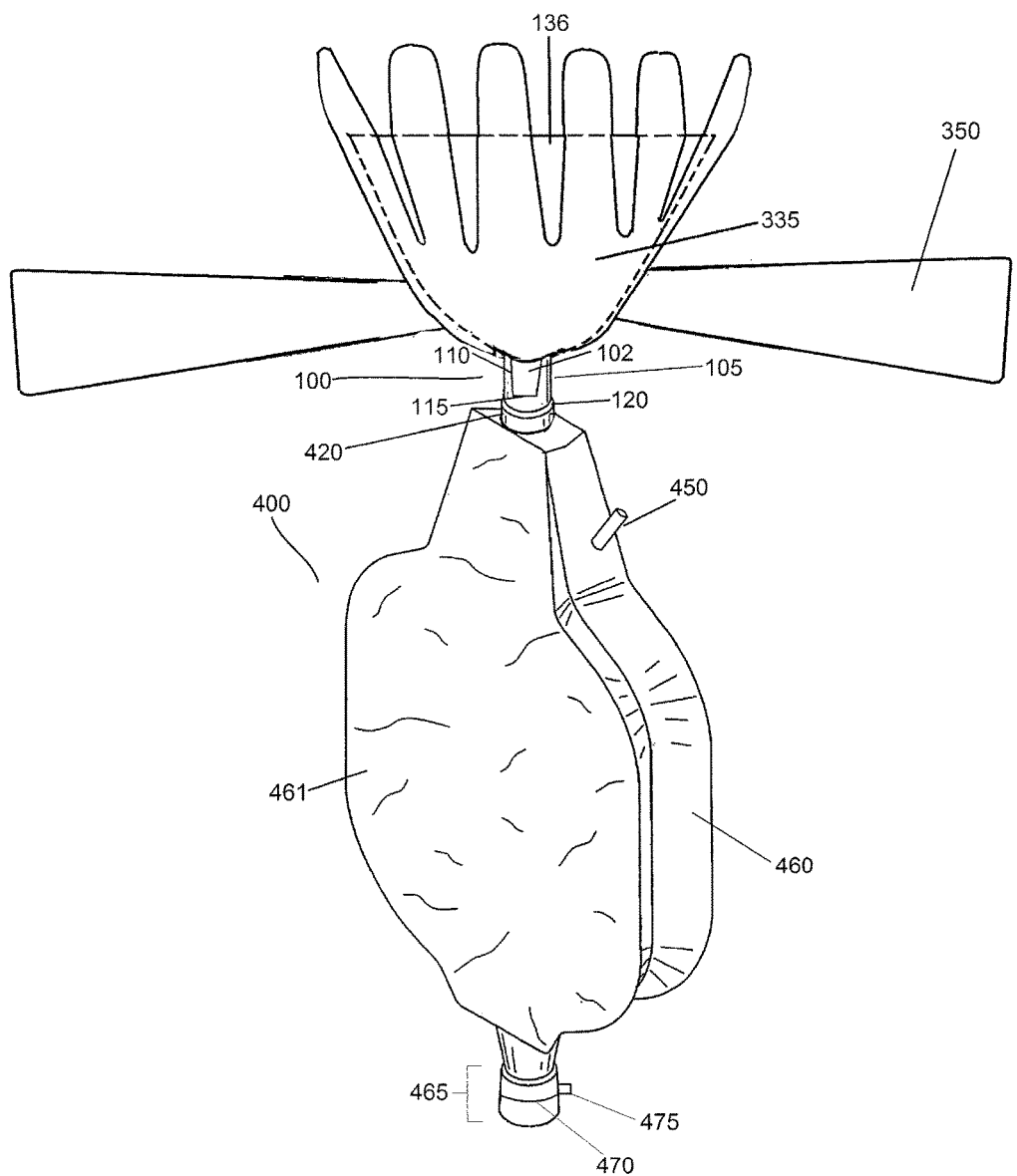
FIG. 5C shows a perspective view of an incontinence control device according to some embodiments of the present invention.

FIG. 5C shows a further exemplary embodiment of the incontinence collection device that includes a collection member 100, a collection receptacle 400, and an adhesive attachment member. As in the embodiment shown in FIG. 5B, the collection member 100 is attached to collection receptacle 400 via the coupling of distal connector 125 to connector 420. The embodiment of FIG. 5C further includes an adhesive attachment member 300 attached to the outer wall of the concave receiver 136. In this embodiment, the adhesive flaps 335 and adhesive straps 350 may assist in attaching and securing the incontinence collection device to the user. In some implementations, and without limitation, the concave receiver 136 may or may not have an adhesive material therein, and the incontinence collection device may be adhered to the penis by the adhesive flaps 335 and an adhesive straps 350 alone. In further embodiments, the adhesive flaps 335 or the adhesive straps 350 may be selective omitted from the incontinence collection device.

Figure 5D:
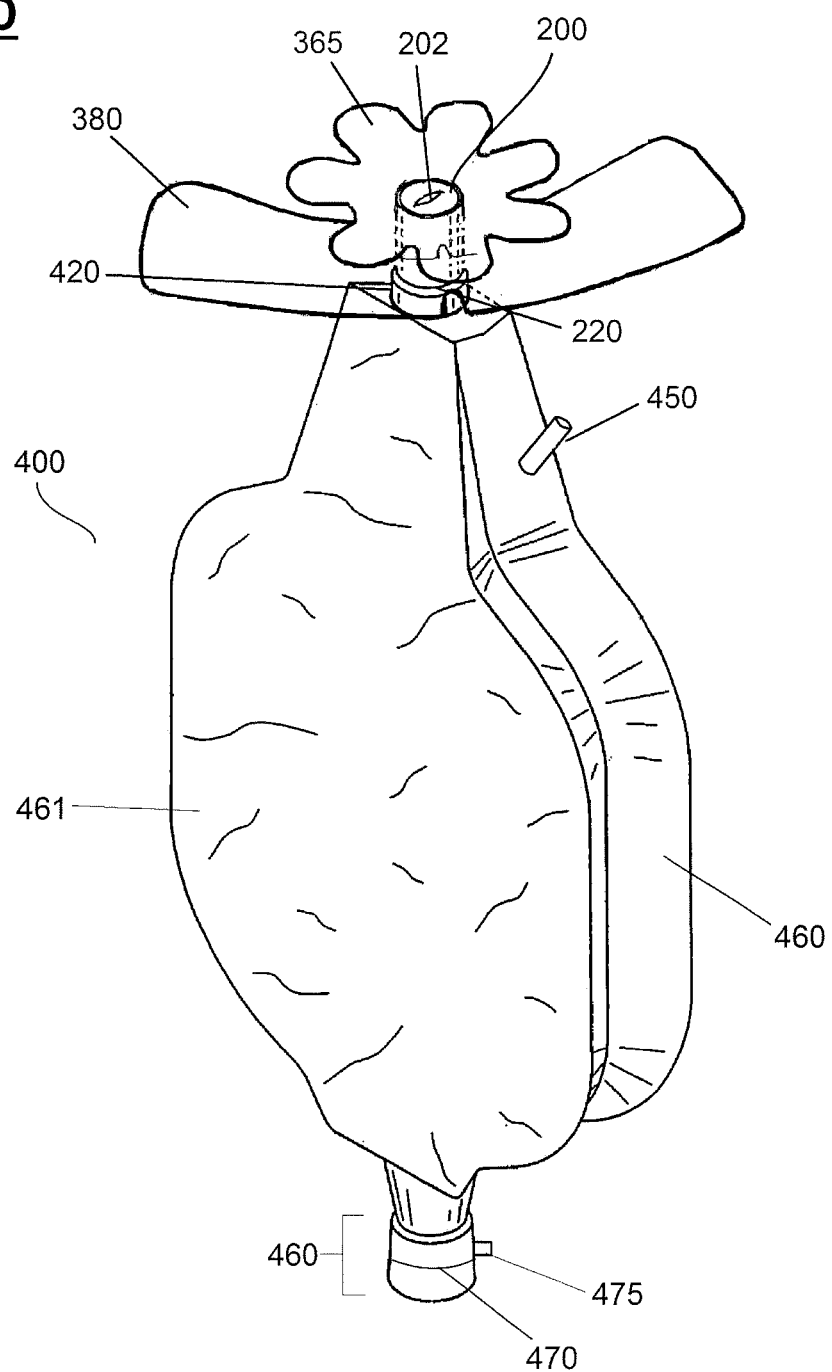
FIG. 5D shows a perspective view of an incontinence control device according to some embodiments of the present invention.

FIG. 5D is a further exemplary embodiment of the incontinence collection device of the present invention in which the collection member 200 is attached to the collection receptacle 400 and the adhesive attachment member 360. The collection member 200 is attached to collection receptacle 400 via the coupling of connector 225 to connector 420. The adhesive attachment member 360 is engaged to and secured to the collection disk 201 of the collection member 200. To attach the collection member 200 to the adhesive attachment member 360 the collection disk 201 may be passed on its side through hole 370 (including the lateral slots in hole 370) in the adhesive attachment member 360. Once the collection disk 201 is passed through hole 370, the posterior side of the collection disk 201 may be secured to the adhesive area 375, thereby providing a stable reliable connection between the adhesive attachment member 360 and the collection member 200. The adhesive flaps 365 and adhesive straps 380 may then be used to attach the incontinence control device to the penis.

Figure 6A:
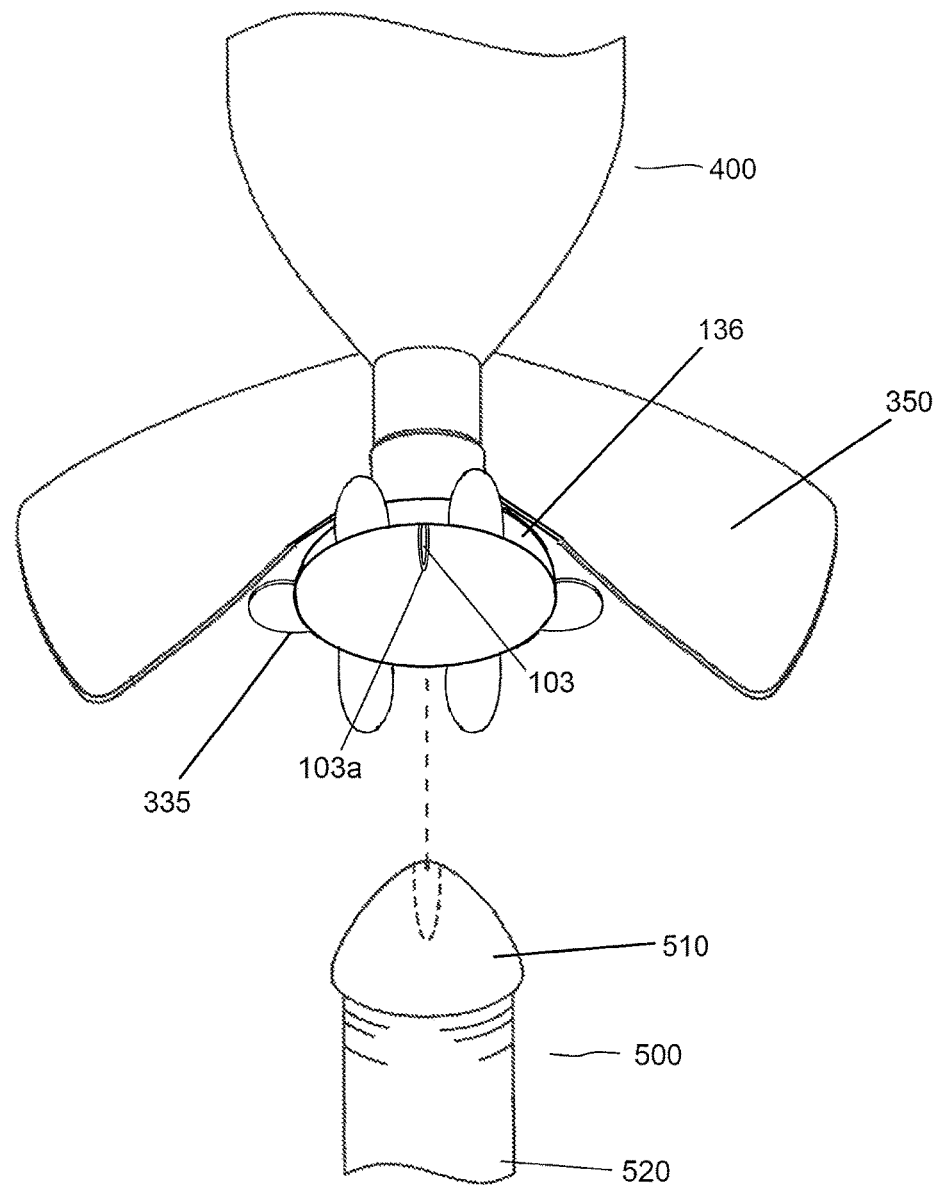
FIG. 6A shows a perspective view of a step in the process of attaching an incontinence control device according to some embodiments of the present invention.
Figure 6B:
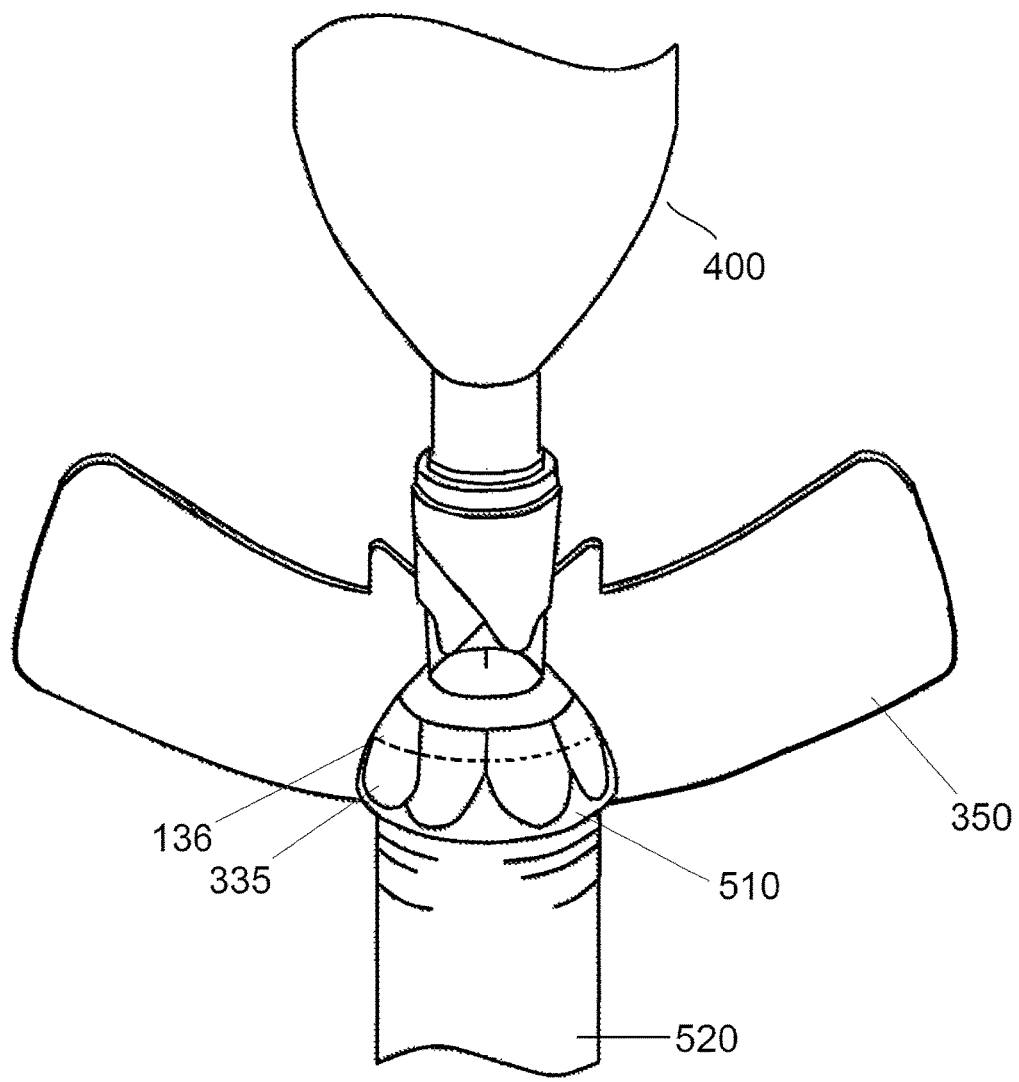
FIG. 6B shows a perspective view of a step in the process of attaching an incontinence control device according to some embodiments of the present invention.
Figure 6C:
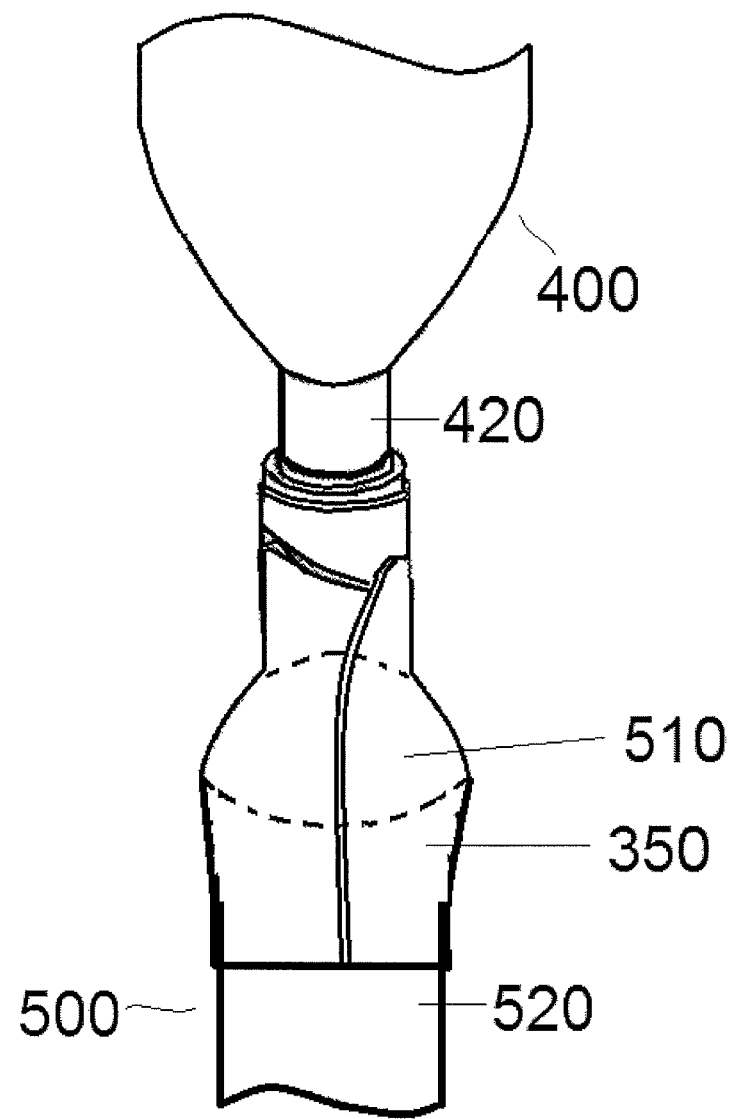
FIG. 6C shows a perspective view of a step in the process of attaching an incontinence control device according to some embodiments of the present invention.

FIGS. 6A-6C show an exemplary process for securing the incontinence collection device of the present invention to the penis. It is to be appreciated that the process shown in FIGS. 6A-6C is exemplary, and that other embodiments of the incontinence collection device (e.g., the embodiment of FIG. 5A) may be attached to the penis 500 using fewer attachment structures than shown in FIGS. 6A-6C. As shown in FIG. 6A, the glans penis 510 may be aligned with the raised bead 103a of the concave receiving member 136, such that the external urethral orifice is aligned with collection hole 103. FIG. 6A shows a dashed line on the glans penis 510 where the raised bead 403a may be positioned. The concave receiving member 136 may include an adhesive such that the user may secure the concave receiving member 136 to the glans penis 510 once the collection hole 103 is aligned with the external urethral orifice.

As shown in FIG. 6B, adhesive flaps 335 may subsequently be attached to the penis 500 proximally relative to the concave receiving member 136 (e.g., on the glans penis 510 and/or the body 520 of the penis) to provide further strength to the connection between the incontinence control device. However, it is to be understood that certain structures may be omitted in some embodiments. For example, the adhesive flaps 335 may be omitted and the incontinence collection device may be attached by the concave receiver 136 and the adhesive straps 350 alone, as shown in the embodiment shown in FIG. 5A.

As shown in FIG. 6C, the adhesive straps 350 may subsequently be wrapped around and attached to the penis 500. The adhesive straps 350 may in part overlap with the concave receiver 136 and/or the adhesive flaps 335, and they may also attach to the penis 500 proximally relative to the concave receiving member 136 and the adhesive flaps 335 (e.g., on the glans penis 510 and/or the body 520 of the penis) to provide further strength to the connection between the incontinence collection device. It is to be appreciated that not all attachment structures must be present and not all attachment structures must have adhesive (e.g., in some embodiments, the concave receiving device may have adhesive solely on the raised bead 103a). It is to be appreciated that FIGS. 6A-6C are not meant to limit the invention to having all of the described attachment members. Rather, the figures have been provided and described to illustrate a preferred embodiment of the present invention.

FIGS. 7A-7E show a devices and techniques for securing the incontinence collection device to the user, such that the user can comfortably wear the incontinence collection device during movement and activity. The present invention may include an undergarment that includes a detachable sleeve into which the collection receptacle of the incontinence collection device may be inserted. The detachable sleeve may include an attachment mechanism for engaging and supporting the weight of the incontinence collection device, preventing detachment of the incontinence collection device from the user, and reduce discomfort that may result from walking or other motion.

Figure 7A:
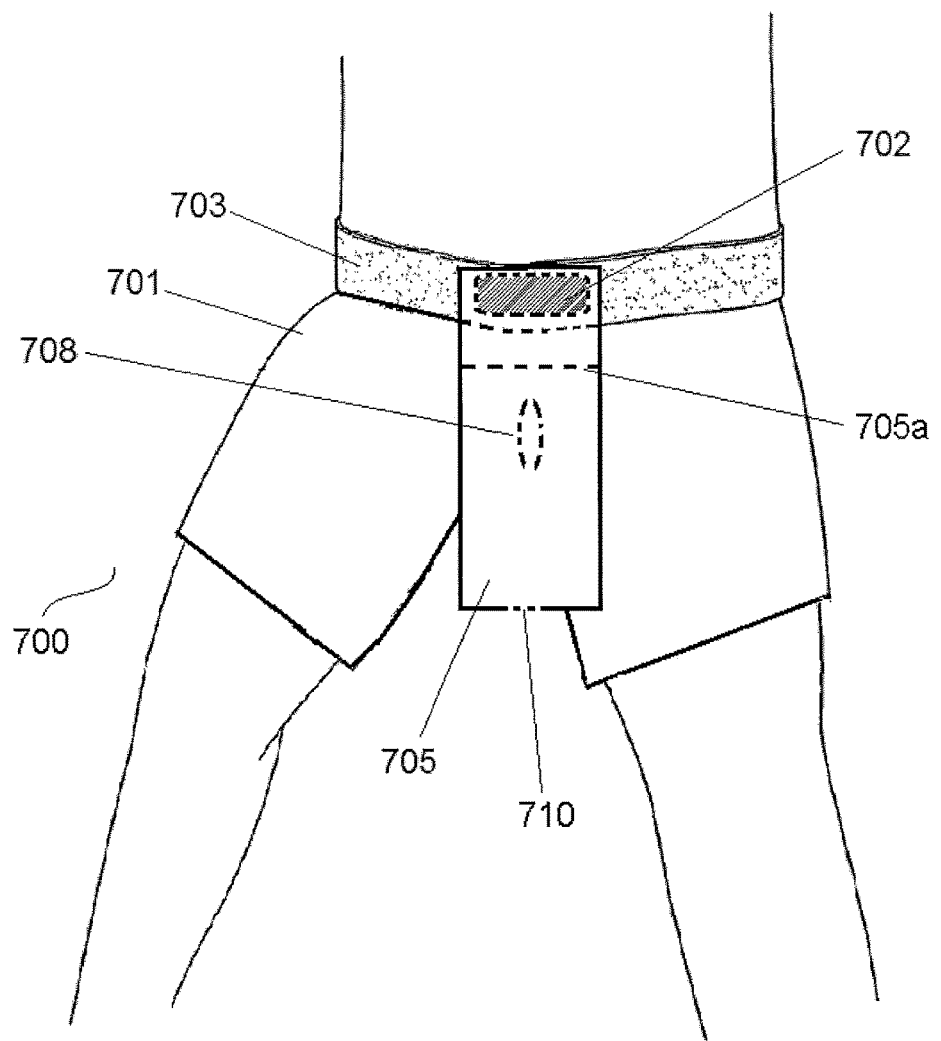
FIG. 7A shows a perspective view of an undergarment according to some embodiments of the present invention.
Figure 7B:
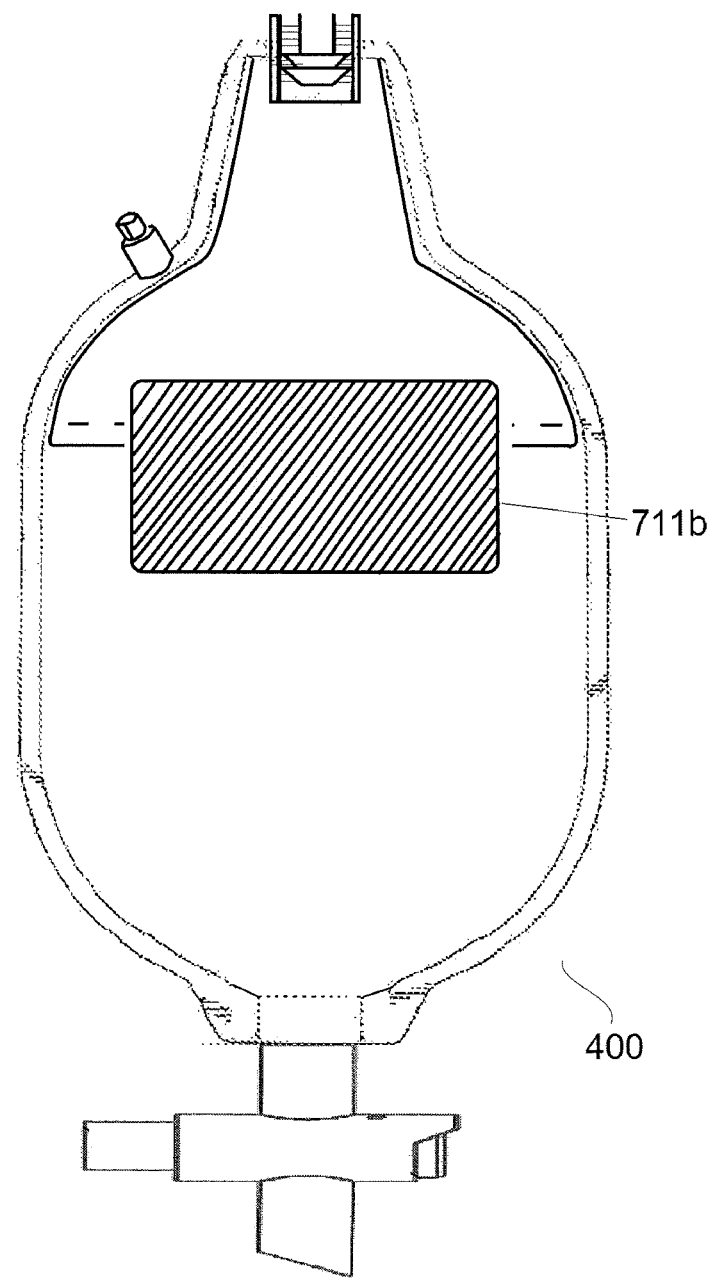
FIG. 7B a frontal view of a collection receptacle with a drainage valve according to some embodiments of the present invention.
Figure 7C:
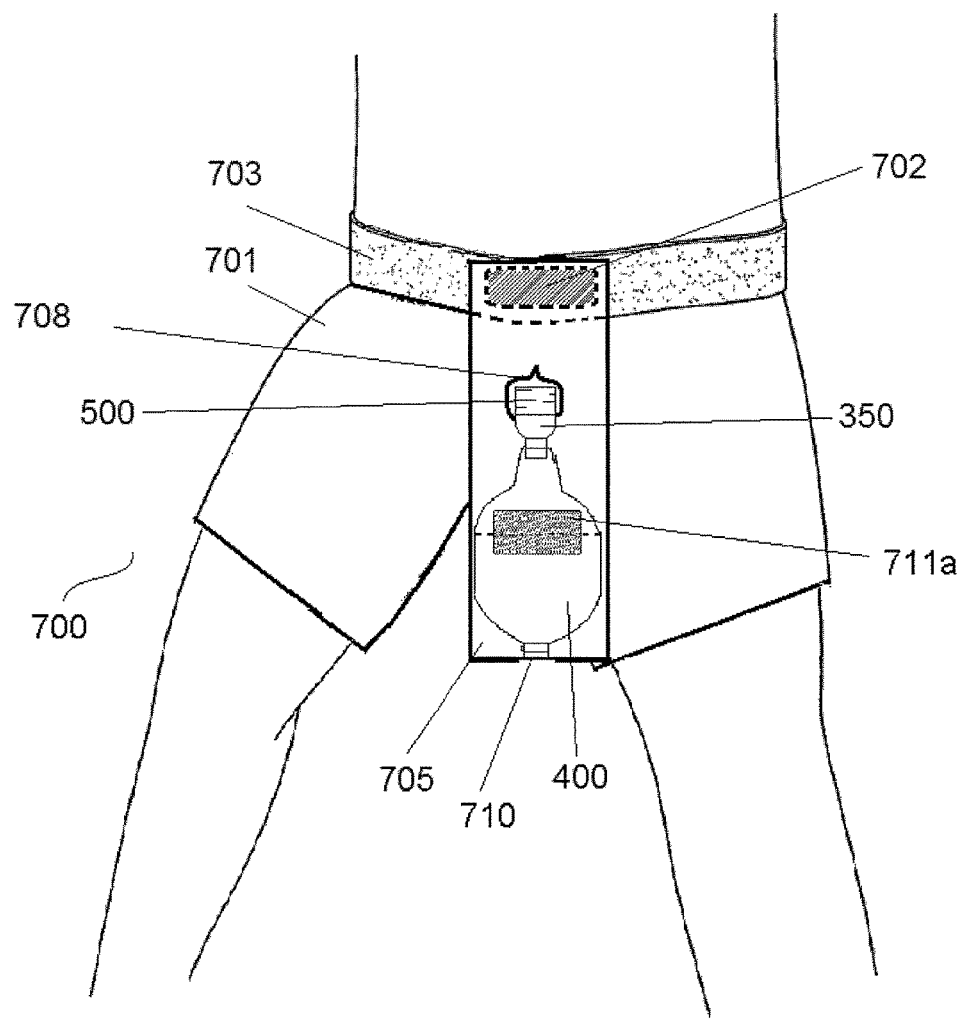
FIG. 7C shows a perspective view of an undergarment according to some embodiments of the present invention.

As shown in FIGS. 7A-7C, the undergarment 700 may have a boxer-short or boxer-brief-like design having legs 701, a waistband 703, and a 2"-3" slit 708 through which the penis may protrude with the incontinence collection device attached thereto. A sleeve 705 may be detachably connected to the waist band 703 or other superior portion of the undergarment 700 by an attachment mechanism 702, such as a fabric hook-and-loop fastening mechanism (e.g., Velcro) having a first fastening panel on the waistband 703 made up of semi-rigid hooks and a second fastening panel on the superior portion of the detachable sleeve 705 made up of soft fabric loops. When the two sides of the hook-and-loop fastening mechanism are brought together the hooks engage with the loops and hold the two sides together. The detachable sleeve 705 may have an open proximal end 705*a* through which the collection receptacle may be passed, and an attachment mechanism 711 for attaching the collection receptacle to the interior of the detachable sleeve 705. The attachment mechanism 711 may be a hook and loop mechanism, where there is a first attachment panel 711*a* on the interior of the detachable sleeve 705 made up of semi-rigid hooks and a second attachment panel 711*b* on the collection receptacle made up of soft fabric loops. The second attachment panel 711*b* may be positioned on the proximal end of the collection receptacle 400, allowing the collection receptacle 400 to hang from the hook/loop attachment on its proximal end.

The distal end of the detachable sleeve 705 may have an opening 710 through which the drainage valve of the incontinence control device may be accessed. The distal opening 710 may allow the user to drain the collection receptacle 400 conveniently without having to remove any portion of the undergarment 700 or dismantle the incontinence control device.

Figure 7E:
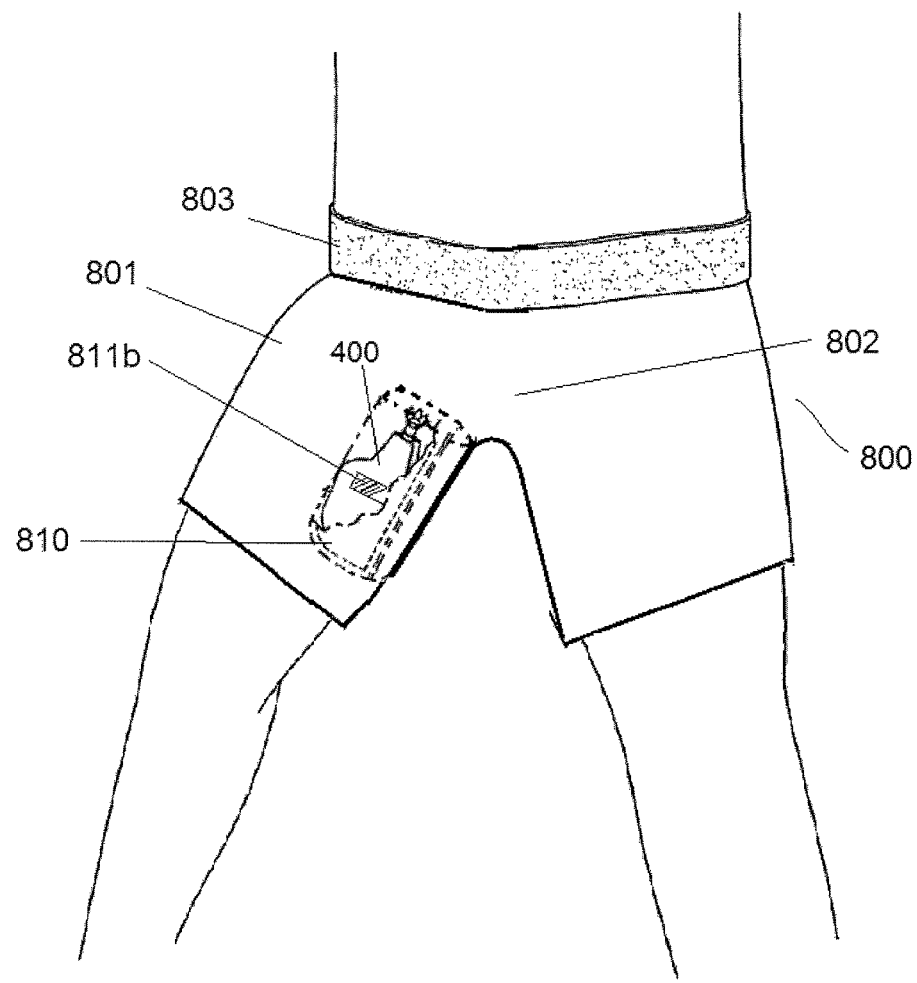
FIG. 7E shows a perspective view of an undergarment according to some embodiments of the present invention.

FIGS. 7D-7E show an alternative undergarment for securing the incontinence control device to the user. The undergarment 800 may have a boxer-short or boxer-brief-like design having legs 801, undercarriage 802, and a waistband 803. The undergarment 800 also may include a pouch 810 for receiving and supporting the collection receptacle 400 of the incontinence control device, which may be located on the interior of the undergarment 800.

The pouch 810 may include a securing mechanism 811 for attaching and securing the collection receptacle 400 within the pouch 810. For example, the securing mechanism 811 may be a fabric hook-and-loop fastening mechanism having a first fastening panel within the pouch 810 and a second fastening panel on the proximal portion of the collection receptacle 400 (as shown in FIG. 7B). In other embodiments, the collection receptacle 400 may be attached and secured to the pouch 810 by other fastening mechanisms such as snap buttons, a flap that closes over the pouch and seals by button(s) or other mechanisms, or other fastening members. As shown in FIGS. 7D-7E, the pouch 810 may include a fastening panel 811*a* and the collection receptacle 400 may include a complementary fastening panel 811*b*. When the collection receptacle 400 is inserted into the pouch 810, the fastening panel 811*b* may be aligned and connected with the fastening panel 811*a* within the pouch 810, such that the collection receptacle 400 is securely hung in the pouch 810 and will not dislodge from the pouch 810 when the user walks or engages in other movements.

FIG. 7E shows the undergarment 800 with the collection receptacle 400 positioned inside of the pouch 810. The complementary fastening panels 811*a* and 811*b* are aligned with and secured to one another to maintain the position of the collection receptacle 400 within the pouch 810. It is to be understood that the undergarment 800 may include different mechanisms for supporting the collection receptacle, e.g., the undergarment may include one or more straps that pass through one or more loops on the collection receptacle to fasten the collection receptacle in position. Such variations are within the scope of the present invention, which is not limited to the examples provided in the drawings.

CONCLUSION

The present invention provides a novel external male incontinence collection device, which allows the user to attach the device in an optimal position. Furthermore, the present invention features an internal one-way valve system within the collection conduit that prevents backflow of urine from a urine receptacle. The one-way valve system prevents the backflow of and the dissolution of the adhesive attaching the device to the user. Furthermore, novel exit valves have been described in the present application that allow for the easy release and drainage of urine from the incontinence collection device.

It is to be understood that variations, permutations, and modifications of the present invention may be made without departing from the scope thereof. One or more features of an exemplary embodiment as described above may be practiced in conjunction with other exemplary embodiments as described above. It is also to be understood that the present invention is not to be limited by the specific embodiments disclosed herein, but only in accordance with the appended claims when read in light of the foregoing specification.

What is claimed is:

1. An incontinence collection device, comprising:
   a. an attachment member having an exit hole for allowing the passage of urine, wherein said attachment member is operable to attach to a distal end of a penis;
   b. a collection member in fluid communication with said attachment member;
   c. a collection receptacle in fluid communication with said collection member, said collection receptacle comprising a one-way valve; and
   d. an exit conduit in fluid communication with said collection receptacle, said exit conduit comprising a drainage valve comprising:
      i. a compressible bulb having a drainage hole; and
      ii. a resilient, flexible actuator comprising a piston member mechanically connected to at least two resilient arms and a plug operable to seal said drainage hole, said two resilient arms being in contact with an interior of said compressible bulb.

2. The device of claim 1, further comprising a securing garment operable to attach to a portion of the user's body and having a sleeve for holding said collection receptacle.

3. The device of claim 2, wherein said securing garment has an attachment mechanism for securing said collection receptacle in position in said sleeve.

4. The device of claim 1, wherein said collection member includes a concave receiver operable to engage with said end of said penis.

5. The device of claim 4, wherein said concave receiver has a raised bead on the interior thereof that surrounds said exit hole.

6. The device of claim 1, wherein said attachment member further comprises at least one adhesive strap extending from said concave receiver for attaching to said penis.

7. The device of claim 1, wherein said collection receptacle comprises an air relief valve, said air relief valve being operable to allow air to pass through said air relief valve.

8. The device of claim 1, wherein said one-way valve has dual membranes that are flexible and comprise distal ends which are intermittently bonded together to reduce backflow of urine from said collection receptacle.

9. The device of claim 1, wherein said collection member comprises a second one-way valve for preventing backflow from said collection member.

10. The device of claim 9, wherein said second one-way valve comprises flexible dual membranes with distal ends intermittently bonded together.

11. The device of claim 1, wherein each arm of said at least two resilient arms comprises a flexible elbow.

12. The device of claim 11, wherein said drainage valve has a closed configuration and an open configuration, and
   a. in said closed configuration said actuator is in a relaxed conformation wherein said elbow in each of said at least two resilient arms is at a first angle when no external force is applied to said pinch valve, and said plug is engaged with said drainage hole, and
   b. in said open configuration an external force is applied to said compressible bulb and said elbow in each of said resilient arms is at a second angle that is greater than said first angle, and said plug is retracted from engagement with said drainage hole.

13. An incontinence collection device, comprising:
   a. a collection receptacle in fluid communication with a collection member for collecting urine; and
   b. a drainage conduit for draining fluid from the collection receptacle;
   c. a drainage valve in fluid communication with the drainage conduit, wherein said drainage valve is a pinch valve comprising:
      i. a compressible bulb having a drainage hole; and
      ii. an actuator that includes
         1. at least two resilient arms, and
         2. a piston member mechanically connected to said at least two resilient arms, and having a plug at a distal end of said piston member, wherein said plug is operable to seal said drainage hole.

14. The device of claim 13, further comprising an attachment member being operable to connect said incontinence collection device with the end of a penis, and a collection member connected to said attachment member.

15. The device of claim 13, wherein said at least two resilient arms being in mechanical connection with an interior of said compressible bulb.

16. The device of claim 13, further comprising a securing garment operable to attach to a portion of the user's body, said securing garment having a sleeve for holding said collection receptacle, and an attachment mechanism for securing said collection receptacle in position in said sleeve.

17. The device of claim 13, wherein said attachment member further comprises at least one adhesive flap for attaching to said penis.

18. The device of claim 13, wherein said collection receptacle comprises a one-way valve having flexible dual membranes intermittently bonded together at distal ends thereof.

19. The device of claim 14, wherein said collection member comprises a one-way valve in said collection member having flexible dual membranes intermittently bonded together at distal ends thereof for preventing backflow.

20. An incontinence collection device, comprising:
   a. an attachment member having an exit hole for allowing the passage of urine; and
   b. a collection receptacle in fluid communication with said attachment member, said collection receptacle including a drainage conduit operable to drain fluid from said collection receptacle and a drainage valve to allow a wearer to control drainage of fluid from said collection receptacle, said drainage valve including a flexible valve mechanism comprising a flexible, extensible actuator that extends longitudinally when compressed and withdraws a plug from a drainage hole of said drainage valve.

21. The device of claim 20, further comprising a securing garment operable to attach to a portion of the user's body and having a sleeve for holding said collection receptacle.

22. The device of claim 20, wherein said securing garment has an attachment mechanism for securing said collection receptacle in position in said sleeve.

23. The device of claim 20, wherein said collection receptacle comprises a one-way valve having flexible dual membranes intermittently bonded together at distal ends thereof.

* * * * *